(12) United States Patent
Caprioli et al.

(10) Patent No.: US 8,697,447 B2
(45) Date of Patent: Apr. 15, 2014

(54) CLEAVABLE SURFACTANTS AND METHODS OF USE THEREOF

(75) Inventors: Richard M Caprioli, Brentwood, TN (US); Ned A. Porter, Franklin, TN (US); Jeremy L. Norris, Smyrna, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 12/946,652

(22) Filed: Nov. 15, 2010

(65) Prior Publication Data

US 2011/0217783 A1    Sep. 8, 2011

Related U.S. Application Data

(62) Division of application No. 11/456,066, filed on Jul. 6, 2006, now abandoned, which is a division of application No. 10/479,477, filed as application No. PCT/US02/16640 on May 28, 2002, now Pat. No. 7,074,936.

(60) Provisional application No. 60/294,337, filed on May 29, 2001.

(51) Int. Cl.
| | | |
|---|---|---|
| *G01N 1/40* | (2006.01) | |
| *G01N 33/49* | (2006.01) | |
| *C07C 305/04* | (2006.01) | |
| *C07C 211/02* | (2006.01) | |
| *C07F 9/54* | (2006.01) | |
| *C07F 7/08* | (2006.01) | |
| *C07F 7/10* | (2006.01) | |

(52) U.S. Cl.
USPC .................................. 436/17; 436/8; 436/177

(58) Field of Classification Search
USPC ........ 436/8, 17, 177; 556/436, 465; 588/8, 32
See application file for complete search history.

(56) References Cited

U.S. PATENT DOCUMENTS

| | | | |
|---|---|---|---|
| 4,713,486 A | | 12/1987 | Buckle |
| 5,099,051 A | * | 3/1992 | Beck et al. .................... 556/401 |
| 5,114,851 A | | 5/1992 | Porter et al. |
| 5,179,224 A | | 1/1993 | Takaki et al. |
| 5,218,137 A | | 6/1993 | Porter et al. |
| 5,808,300 A | | 9/1998 | Caprioli |
| 6,306,249 B1 | | 10/2001 | Galante et al. |

FOREIGN PATENT DOCUMENTS

| | | | |
|---|---|---|---|
| CN | 1280132 A1 | * | 1/2001 |
| DE | 2943750 A1 | * | 5/1980 |
| DE | 3728917 A1 | * | 3/1989 |
| JP | 5105621 | | 4/1993 |
| WO | 0070334 | | 11/2000 |
| WO | 02097393 | | 12/2002 |

OTHER PUBLICATIONS

Pankaskie, M. et al. "Inhibitors of polyamine biosynthesis VII: Evaluation of pyruvate derivatives as inhibitors of S-adenosyl-L-methionine decarboxylase." Journal of Pharmaceutical Sciences (1980) 69 1000-1004.*
Nam, et al.; Sytheses of certain 3-aryl-2-propenoates and evaluation of their cytooxicity; Bioorg. Med. Chem. Letters 11; 2001; pp. 1173-1176.
Hori, et al.; Inhibition of tyrosine kinase and src oncogene functions by stable erbstatin analogues; The J. of Antibiotics; 45(2); 1992; pp. 280-282.
Nguyen, et al.; Synthesis and antitumor activity of alkyl 2, 5-dihydroxycinnamates; 2002; Abstract.
Hazard, et al.; Electrochemical preparation of N-hydroxyindoles. II. Controlled potential oxidation of some .alpha. -(o-hydroxyaminophenyl)alkenes; 1974; Abstract.
Beilstein Institut Zur Foerderung Der Chemischen Wissenschaften, Frankfurt Am Main, DE; 27(15); 1997; pp. 2651-2682; Abstract.
Norris, et al.; Combination detergent/MALDI matrix: Functional cleavable detergents for mass spectrometry; Analytical Chemistry; Aug. 1, 2005; 77(15); pp. 5036-5040.
Norris, et al.; Nonacid cleavable detergents applied to MALDI mass spectrometry profiling of whole cells; Journal of Mass Spectrometry; 2005; 40; pp. 1319-1326.
Behforouz, et al.; Alkyl and Aryl Sulfenimides; J. Org. Chem..; 34 (1); 51-55; 1969.
Guyot, et al., Esterification of phenolic acids from green coffee with an immobilized lipase from *Candida antarctica* in solvent-free medium; Biotechnology Letters; vol. 19. No. 6; Jun. 1997; pp. 529-532.
Harpp, et al.; A New Synthesis of Unsymmetrical Disulifdes; Tetrahedron Letters; 41; pp. 3551-3554; 1970.
Kyte, et al.; J. Mol. Biol.; 1982; 157(1):105-32.
Laemmli; Nature 227; 680-685; 1970.
Smith, et al.; March's Advanced Organic Chemistry: Reactions, Mechanisms, and Structure; 5th Ed.; pp. 1-1824, 2001.
Wuts, et al.; Protective Groups in Organic Synthesis; 1999; 3rd Ed.; 1-779.

* cited by examiner

*Primary Examiner* — Christopher A Hixson
(74) *Attorney, Agent, or Firm* — Stites & Harbison PLLC; Richard S. Myers, Jr.

(57) ABSTRACT

The present invention includes a cleavable surfactant/detergent compound of the following formula:

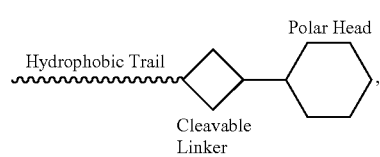

wherein the variables are defined herein. Embodiments of the cleavable surfactant/detergent compound are useful, for example, in methods for isolating a hydrophobic molecule that include providing a plasma comprising a hydrophobic molecule, applying the cleavable surfactant to the plasma so that the surfactant engages the hydrophobic molecule, cleaving the surfactant from the hydrophobic molecule, and analyzing said hydrophobic molecule.

3 Claims, 7 Drawing Sheets

CLEAVABLE SURFACTANTS AND METHODS OF USE THEREOF

RELATED APPLICATIONS

This application is a divisional application claiming benefit to U.S. patent application Ser. No. 11/456,066 filed Jul. 6, 2006, now abandoned, which is a divisional of U.S. patent application Ser. No. 10/479,477 filed Dec. 1, 2003, now issued under U.S. Pat. No. 7,074,936, which claims priority under 35 U.S.C. §371 of PCT/US02/16640, filed May 28, 2002, which in turn claims priority to U.S. patent application Ser. No. 60/294,337, filed May 29, 2001. All of the prior applications are incorporated herein by reference in their entirety.

FIELD OF THE INVENTION

The present invention relates generally to cleavable detergents or surfactants and methods of use thereof including sample isolation, solubilization, emulsification, and analysis. Furthermore, the present invention relates to cleavable surfactants which are useful for sample preparation, but which can be cleaved for removal or to yield cleavage products which have additional useful properties, including for matrix assisted laser desorption ionization mass spectroscopy (MALDI MS) analysis of hydrophobic molecules including natural and synthetic polymers and polypeptides.

The cleavable detergents or surfactants of the present invention, among other things in additional embodiments, improve the quality of MALDI MS analyses of proteins, including high molecular weight proteins associated with biological tissue.

BACKGROUND OF THE INVENTION

Proteomics, the study of proteins and their functions, is currently a focus of both university and commercial investment as each discovery in proteomics holds the potential to unlock yet another advance in medical science. The extreme variability in the chemistry of proteins in biological systems and especially in mammals, presents special problems.

A recurring problem with respect to proteomics involves the poor solubility of a large percentage of proteins such as those found in lipid membranes and other hydrophobic areas of the cell or in the cellular environment. This is because many of the systems developed for the study of proteins are geared to analysis in an aqueous environment. To isolate hydrophobic proteins or hydrophobic protein domains, surfactants (detergents, such as sodium dodecyl sulfate (SDS) or triton X) are commonly employed. Surfactants generally have a polar head group and a hydrophobic tail group and encapsulate hydrophobic proteins wherein the hydrophobic tail is in contact with the hydrophobic protein and the polar groups are in contact with the water. Thus, hydrophobic proteins and polypeptides are sequestered in a coating of detergent wherein the complex is soluble in an aqueous environment.

However, many analytical systems are sensitive to the presence of surfactants. For example, SDS and triton X suppress the analyte signal during matrix assisted laser desorption ionization mass spectrometry (MALDI MS) analysis. Signal suppression from surfactant contamination is contemplated to result from physical and chemical blockage of the ionization/desorption process of MALDI MS.

What is needed are surfactant compositions and methods suitable for MALDI-MS analyses, and other analyses, of hydrophobic molecules including natural and synthetic polymers and polypeptides/proteins.

International Publication WO 00/70334 to Lee et al., discloses certain surfactants and results for electrospray mass spectroscopy (MS) analysis of myoglobin in the presence of certain of the surfactants.

U.S. Pat. No. 4,713,486 to Buckle discloses certain arachidonic acid analogues, including certain cinnamates, stated to be useful in the treatment of allergic diseases.

U.S. Pat. No. 5,114,851 to Porter et al., discloses certain light activated acyl-enzymes.

U.S. Pat. No. 5,218,137 to Porter et al., discloses certain compounds useful as an intermediate for making light-activatable acyl-enzymes.

Also see U.S. Pat. No. 5,808,300 to Caprioli, incorporated herein by reference, for a discussion of MALDI MS.

Additional background information may be found in the following publications: Kyte et al., J. Mol. Biol. (1982) 157(1):105-32; March's Advanced Organic Chemistry: Reactions, Mechanisms, and Structure, 5th Ed. by Michael B. Smith and Jerry March, John Wiley & Sons, Publishers; Wuts et al. (1999) Protective Groups in Organic Synthesis, 3rd Ed., John Wiley & Sons, Publishers; Behforouz, M.; Kerwood, J. E. *Alkyl and Aryl Sulfenimides*. J. Org. Chem., 34 (1), 51-55 (1969); and Harpp, D. N.; Ash, D. K.; Back, T. G.; Gleason, J. G.; Orwig, B. A.; VanHorn, W. F. *A New Synthesis of Unsymmetrical Disulifdes. Tetrahedron Letters,* 41, 3551-3554 (1970).

SUMMARY OF THE INVENTION

This invention relates to the treatment of a sample, such as a tissue section from a plant or animal, with a compound or mixture of compounds that would perform multi-functional roles in the preparation of these samples for analysis, e.g., mass spectrometry or chromatography, at designed times determined by treatment conditions. These compounds would be able to function as a surfactant or detergents in helping solubilize hydrophobic or other non-soluble compounds. Due to built in cleavable bonds, appropriate treatment of the sample, for example, with acid, base, heat, light, etc., would then cause decomposition of the agent to two or more smaller parts, each of which does not materially interfere with the analysis. Further, each part may in itself perform a further function; for example, one part may help solubilize compounds present in the mixture and the other, for MALDI mass spectrometry, may form crystals in the same way matrix acts in common MALDI analysis.

Accordingly, the present invention provides, in part, compositions and methods including, but not limited to: novel cleavable surfactants and methods for preparing cleavable surfactants and using them in proteomic analysis including for matrix assisted laser desorption ionization mass spectrometry (MALDI MS). Certain compositions disclosed herein include the surprising properties of being a surfactant that yields one or more analyte assisting molecules upon cleavage including a MALDI matrix composition and a volatile solvent. No aspect or embodiment of the present invention including any claim is bound by theory or mechanism.

In embodiments of the present invention, compounds of the present invention may be constructed or synthesized in two parts, connected by a linking group that can be cleaved by the addition of another chemical agent or energy source. The portion of the compound that would act as a matrix after cleavage would be polar in nature and, in certain embodiments, be a cinnamic acid analog or similar compound. The second part of the molecule may be for example, a hydrophobic molecule such as hexane or octane alkyl group with a functional group such as thiol or alcohol. After cleavage, this compound may act as a solvent, allowing solubilization of other compounds present including the other part of the agent. The linkage between the parts may comprise a bold such as, for example, a disulfide, thio ester, etc. that would preferably be stable until exposed to a chemical or energy source whereby it would cleave into the two parts described above.

Advantages described in certain aspects and embodiments of the present invention include that hydrophobic elements, such as certain polymers, polypeptides, proteins, and components of cell samples, and tissue samples, etc. can be isolated and extracted using a detergent or surfactant and then the surfactant compound is treatable or treated to yield cleavage compositions with different and useful properties. For example, certain novel surfactant compositions described herein lose their surfactant properties upon cleavage of a linker group and the cleavage products are easily removed from the sample especially in comparison to the parent compounds or other surfactants which tend to stick to hydrophobic molecules.

One aspect of the present invention comprises surfactants including a MALDI MS matrix joined to a hydrophobic tail group by a cleavable linker.

Another aspect of the present invention provides cleavable surfactants having a cinnamic group joined to a hydrophobic tail group by a cleavable linker. Still another aspect of the invention provides a sinapinic group and a hydrophobic group joined by a cleavable linker. In certain embodiments, the linker comprises a disulfide group, a thioester group, or a ketal group. In certain preferred embodiments, the linker is a thioester group.

Another aspect of the present invention provides novel cleavable surfactants having a polar head group joined to a hydrophobic tail by at least one cleavable linker.

Another aspect of the invention provides certain novel cleavable surfactants which lose their surfactant properties upon a cleavage.

Still another aspect of the present invention provides methods for using surfactants (novel to this invention or otherwise) for analysis of molecules, proteins, polypeptides, polymers and the like that are hydrophobic or include hydrophobic regions or domains.

In certain embodiments, methods are provided herein for using novel surfactants of the present invention in the preparation of biological samples or polymers for mass spectral analysis and preferably MALDI MS analysis. Advantages of these methods over the prior art is that the surfactants can be cleaved to yield a sample with analyte useful for MALDI MS analysis.

In certain preferred embodiments, methods are provided herein for treating tissue specimens or cell samples (e.g., for preparation or isolation of hydrophobic proteins or other molecules.

The processes of the present invention may include a enzymatic digestion of the hydrophobic protein before or after cleavage of the detergent. In this embodiment, the fragments may then be subjected to MS/MS for sequence analysis and identified using database searching.

Although certain aspects, embodiments, drawings and elements of the invention are described herein, these are meant to be illustrative and not limiting. For example, one of ordinary skill in the art will be able to establish equivalents to certain elements herein, these equivalents are considered to be within the spirit and scope of the present invention.

The cleavable detergents/surfactants of the present invention have been found to increase the signal intensity of high molecular weight proteins in MALDI analyses, and help eliminate the suppressive effects of detergents in MALDI-MS. Additionally, the detergents/surfactants of the present invention increase the number of ions detected in mouse liver tissue extracts, yielding a more complete peptide/protein profile.

BRIEF DESCRIPTION OF THE DRAWINGS

Reference is now made to the accompanying drawings, which form a part of the specification of the present invention.

DETAILED DESCRIPTION OF THE INVENTION

Figure 1:
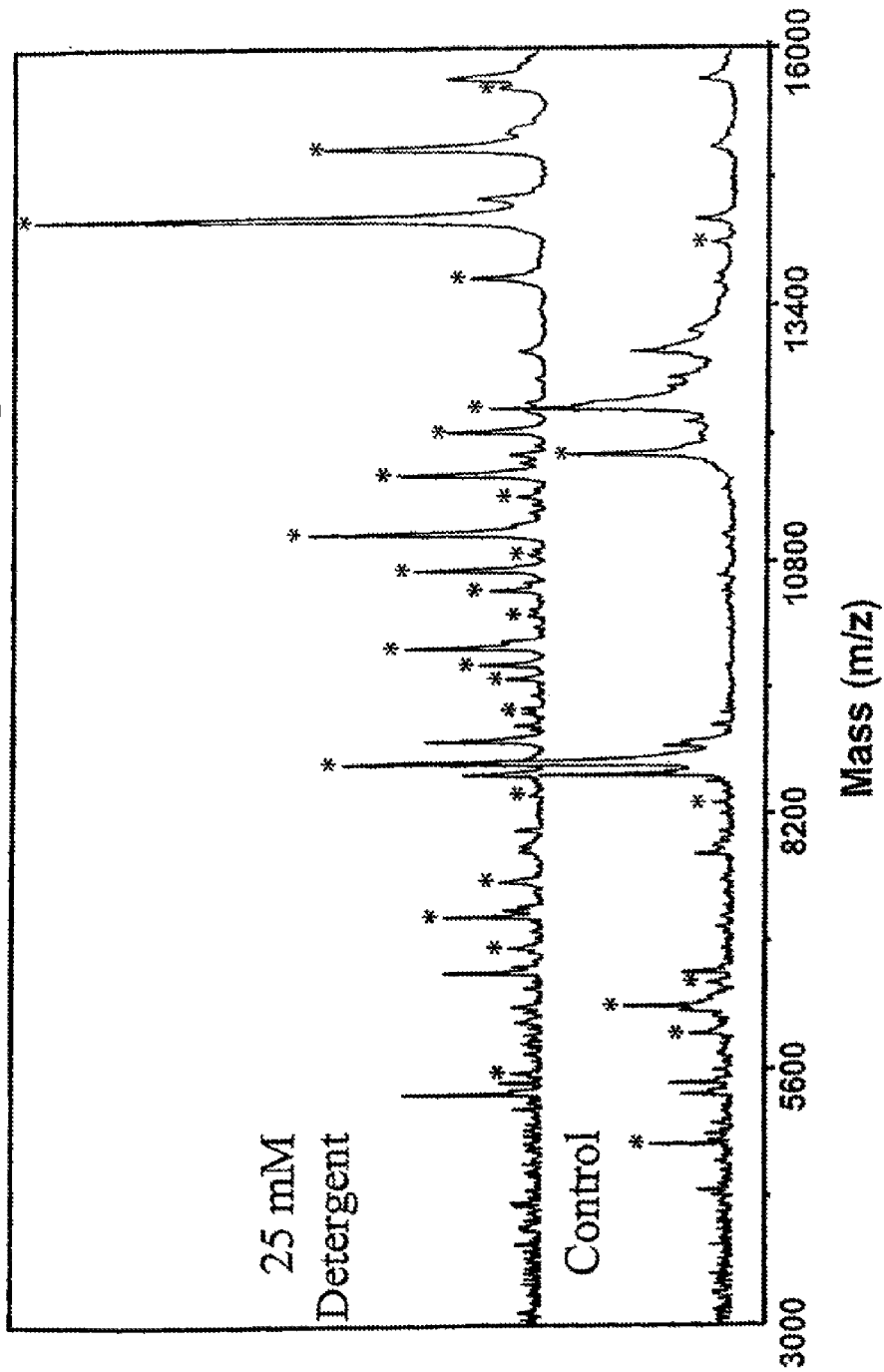
FIG. 1: a chart describing the MALDI mass spectra of a cleavable detergent of the present invention in an analysis of mouse liver.

The present invention solves problems in the prior art associated with analysis of hydrophobic molecules. As indicated, many analytical systems function best when samples are aqueous or the molecules being analyzed in the sample are solubilized in an aqueous environment. For example, mass spectrometry (MS), and particularly matrix assisted laser desorption ionization MS (MALDI MS) is a powerful analytical tool capable of resolving or discriminating between molecules within one or a few atomic units of mass. MS is also exquisitely sensitive with possible detection capabilities in the picomole or even femtomole range.

MS analysis of hydrophobic molecules or molecules with significant hydrophobic regions has proven troublesome. These molecules are difficult, or sometimes essentially impossible, to suspend in aqueous solution. They tend to aggregate and precipitate out of solution as the hydrophobic domains interact in a manner to minimize contact with the aqueous environment of typical MS samples preparations.

Molecules of special commercial importance include hydrophobic polymers, such as certain constituents of plastics; hydrophobic polypeptides, for example membrane associated proteins, receptors; and lipids, lipophillic cellular components, and hydrophilic extracellular components. The typical approach to manipulating such molecules is to apply detergents or surfactants to bring the hydrophobic molecule of interest out of its native environment and into a more aqueous environment. Surfactants generally include a hydrophilic (or polar) head group and a hydrophobic tail. They may arrange about a hydrophobic molecule with the tails interacting with hydrophobic areas on the molecule and the polar head group interacting with water in the environment.

For example, receptor proteins are often associated with or inserted into the plasma membrane of a cell and are generally hydrophobic in nature (at least the lipid associated portions thereof). Surfactants are useful to isolate the receptor protein away from the plasma membrane. However, surfactants are also notorious for disrupting MALDI MS analysis. The addition of common surfactants such as sodium dodecyl sulfate, triton X, and tween essentially eliminates a molecular signal generated by MALDI MS as well as electrospray MS.

The present invention provides compositions and methods that solves these and other problems of the prior art.

1.0 Definitions

Unless otherwise defined, all technical and scientific terms used herein have the same meaning as commonly understood by one of ordinary skill in the art to which this invention pertains. In case of conflict, the present document, including definitions, will control. Descriptions of preferred methods and compositions are provided herein, but should not be construed to be limiting. No aspect, embodiment, or element of the present invention, including the claims, is limited or bound by theory or mechanism of operation.

The terms "peptide", "polypeptide", and "protein" are used interchangeably herein unless a higher order conformation of a polypeptide is stated to be important, then "protein" may indicate the higher order structure while "polypeptide" refers to the amino acid sequence.

The meaning of hydrophobic molecules, including synthetic and natural polymers, is known in the art. When referring to a hydrophobic protein, it is understood that the protein may have a "net" hydrophobicity, this is, overall the protein is more hydrophobic than hydrophilic. Net hydrophobicity is determined using a hydropathic index of amino acids. For example, each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In this example, the more positive values are more hydrophobic. (For example, see Kyte et al., J. Mol. Biol. (1982) 157(1):105-32, incorporated herein by reference)

Hydrophobic proteins are those that have a positive total hydropathic index after the following operation: each amino acid in the polypeptide chain is converted to its respective index value and the values are summed to yield a total hydropathic index. The hydrophobic/non-hydrophobic nature of polypeptides and peptides can likewise be determined. It is understood that certain proteins and polypeptides may have regions that are hydrophobic and that these regions interfere with analysis or usefulness of the molecules, for example, MALDI MS. In these cases, the hydropathic index for the region is of interest and is determined. In certain cases, the region will comprise consecutive amino acids and in other cases the region will comprise a hydrophobic surface brought together by higher order folding of the polypeptide chain (such as, tertiary structure).

Hydrophobic also means "water fearing", from the Greek words hydro—"water" and phobo—"fear." The hydrophobic effect is an entropy driven force that causes oil to separate from water. The hydrophobic force is strong, though not typically as strong as covalent forces. This force is one of the main determinants of the structure of globular protein molecules, since the hydrophilic (water loving) parts of the protein tend to surround the hydrophobic parts that cluster in the center, away from the aqueous (polar) solvent. In other proteins, the hydrophobic regions are exposed, but inserted into or associated with membranes or other hydrophobic structures.

The meaning of a "polar head group" or "hydrophilic group" is known in the art and generally means a group or molecule that is readily soluble in an aqueous environment. The meaning of a "hydrophobic tail", "hydrophobic tail group", or "hydrophobic group" is known in the art and generally refers to a molecule that is not intrinsically soluble in an aqueous environment.

As used herein the terms "emulsifier", "wetting agent", "detergent", and "surfactant" are used interchangeably to mean an agent that reduces a surface tension in water. For example, a surfactant promotes keeping a hydrophobic polypeptide or generally hydrophobic protein in an aqueous solution.

2.0 Introductory Description of Certain Embodiments

Certain novel surfactants are described herein that include a hydrophilic or polar head group connected by one or more covalent bonds to a hydrophobic tail group by at least one cleavable linker Certain novel surfactants of the present invention include a matrix head group, comprising a MADLI matrix, a MALDI matrix precursor, or (in certain embodiments) a derivative of a MALDI matrix. The matrix head group is typically a polar molecule or a polar molecule after cleavage of the cleavable linker. Detergents of the present invention include in certain embodiments, but without limit, zwitterionic detergent, anionic detergent, cationic detergent and non-ionic detergent.

3.0 Cleavable Linkers

Any chemical group (one or more atoms) that combines a polar head group with a hydrophobic tail is contemplated to be useful in certain embodiments of the present invention. In certain embodiments, the interaction between a linker and the head and tail groups can be ionic bonding, hydrogen bonding, and Van der Walls bonds. One or more covalent bonds is preferred. The present invention includes one or more linkers, one or more polar head groups, and one or more hydrophobic tail groups. In certain embodiments, a linker is any chemical group that combines a matrix head group with a hydrophobic tail including, without limit, by formation of any of the above mentioned bonds.

Preferred cleavable linkers include a ketal linkage, a disulfide linkage, and a thioester linkage. In general, disulfide bond linkages are cleaved by applying a reducing agent. For example, dithiothreitol (DTT), β-mercaptoethanol (BMT), hydrogen sulfide ($H_2S$), sodium hydrosulfide (NaSH), acid ($H^+$ in $H_2O$), or base ($OH^-$ in $H_2O$); are useful for cleaving a disulfide linkers of the present invention. In addition, light energy (hv), preferably in the ultraviolet range, is useful for cleaving a disulfide linker of the present invention. In general, ketal linkers are cleaved using acid ($H^+$ in $H_2O$), or in certain embodiments, base ($OH^-$ in $H_2O$). In general, a linker can be formed by synthesizing a cinnamic molecule with an ester in a 1 position of the cinnamic ring and a nucleophilic group (e.g., —OH, or —$NH_2$ without limit) at the 2 position. Either acid or base conditions can be used to cleave such a linker as the ester undergoes nucleophilic attack. In general, thioester linkers are cleaved using reducing agents, acid, or base (see above for examples). In certain preferred embodiments, thioester linkages are used to join a known MALDI matrix as the head group with a hydrophobic tail. This is because cleavage of the thioester linkage, in general, yields an unmodified matrix product along with the hydrophobic tail group (which is generally an aliphatic alcohol). In additional embodiments, thioester linkages are used to join a suspected MALDI matrix or a derivative of a known MALDI matrix

4.0 Cleavable Surfactants

The present invention provides novel surfactants useful for various industries including for manipulation and analysis of plastics and proteomics. In general, it is an object of the present invention that these surfactants are cleavable into non-surfactant or essentially non-surfactant components. (Although, the hydrophobic tail groups might generally be considered to be weak surfactants by some in the art; these do not induce significant MALDI signal suppression and they have distinct advantages over other, especially stronger, surfactants as discussed herein.) One advantage to the cleavable surfactants of the present invention is that the cleavage products are readily removed by standard isolation techniques (e.g., dialysis, ion exchange chromatography, filtration); whereas, non-cleavable surfactants tend to stick to the protein, or other hydrophobic molecules and are difficult to remove from the sample without losing the analyte itself.

In certain preferred embodiments, the surfactant is made up of a hydrophobic group linked by a cleavable linker to a polar group, wherein the polar group is a MALDI MS matrix or precursor thereof. Thus, cleavage of the surfactant results in the liberation or formation of a MALDI matrix, or a derivative of a MALDI matrix in the sample. One advantage to this in certain embodiments, is that the surfactant used to isolate the hydrophobic molecule is cleaved to form the MALDI matrix. The surfactant properties of the parent detergent are lost and MALDI MS analysis can be carried out without surfactant induced signal suppression (or at least a reduction in signal suppression). An additional advantage is that the hydrophobic tail group is typically chosen (see below) to have certain of the following properties: a solvent for the hydrophobic molecule, volatile which supports the formation of superior matrix crystals, and readily removable from the sample if desired (e.g., aliphatic groups such as hexane which generally yields hexanol as synthesized herein or an aromatic such as a benzene which can be drawn off under vacuum).

5.0 Polar Head Groups

In certain general embodiments, the polar head group may be any compound compatible with being joined to the linker, is not a strong surfactant (as defined or determined by testing to see if MALDI signal suppression is observed in the presence of the compound). In certain embodiments, preferred polar head groups comprise a MALDI matrix or a precursor or derivative thereof. In certain highly preferred embodiments, the polar head group includes cinnamic acid, derivatives of cinnamic acid, sinapinic acid, alpha-cyano-4-hydroxycinnamic acid (αCHCA), and 2,5-dihydroxybenzoic acid (2,5-DHB). Examples of certain preferred polar head groups useful for the present invention are described in Table 1, below. The table below list certain embodiments and is not intended to limit the scope of the invention.

TABLE 1

| Name | Molecular Structure | Molecular Formula | Molecular Weight |
|---|---|---|---|
| sinapinic acid (SA) (3,5-dimethoxy-4-hydroxycinnamic acid) | Formula 1 | $C_{11}H_{12}O_5$ | 225.22 |
| alpha-cyano-4-hydroxycinnamic acid (CHCA) | Formula 2 | $C_{10}H_7NO_3$ | 190.18 |
| gentisic acid (DHB) (2,5-dihydroxybenzoic acid) | Formula 3 | $C_7H_6O_4$ | 155.13 |

TABLE 1-continued

| Name | Molecular Structure | Molecular Formula | Molecular Weight |
|---|---|---|---|
| 2',4',6'-trihydroxyacetophenone (THAP) | 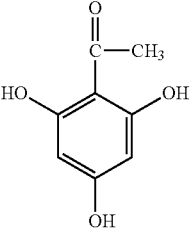<br>Formula 4 | $C_8H_8O_4$ | 186.17 |
| 3-hydroxypicolinic acid (HPA) (3-hydroxy-2-pyridinecarboxylic acid) | 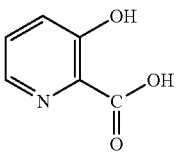<br>Formula 5 | $C_6H_5NO_3$ | 140.12 |
| dithranol (DIT) | 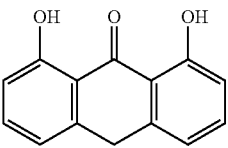<br>Formula 6 | $C_{14}H_{10}O_3$ | 226.06 |
| 2,-(4-hydroxy-phenlyazo)-benzoic acid (HABA) | 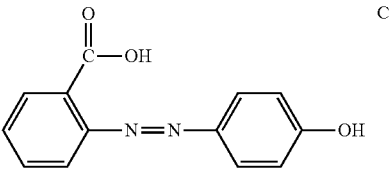<br>Formula 7 | $C_{13}H_{10}N_2O_3$ | 242.23 |
| trans-3-indoleacrylic acid (IAA) | 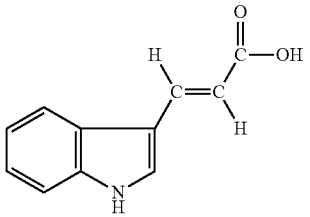<br>Formula 8 | $C_{11}H_9NO_2$ | 187.20 |
| ferulic acid (4-hydroxy-3-methoxycinnamic acid) | 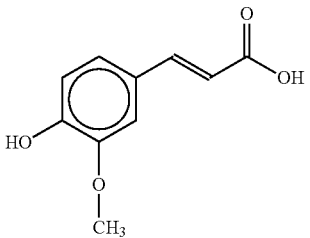<br>Formula 9 | $C_{10}H_{10}O_4$ | 195.20 |

TABLE 1-continued

| Name | Molecular Structure | Molecular Formula | Molecular Weight |
|---|---|---|---|
| nicotinic acid-N-oxide | 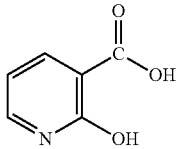 Formula 10 | $C_6H_5NO_3$ | 140.12 |
| 2'-6'-dihydroxyacetophenone | 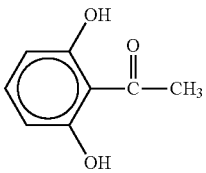 Formula 11 | $C_8H_8O_3$ | 153.16 |
| picolinic acid (PA) (2-pyridine carboxylic acid) | 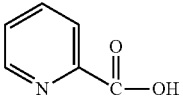 Formula 12 | $C_6H_5NO_2$ | 123.1 |
| 6-aza-2-thiothymine (ATT) | 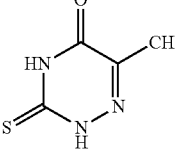 Formula 13 | $C_4H_5N_3OS$ | 143.17 |

6.0 Hydrophobic Tail Groups

In certain general embodiments, the hydrophobic tail is any compound compatible with being joined to the linker, is not a strong surfactant (as defined or determined by testing to see if significant MALDI signal suppression is observed in the presence of the compound). (In certain embodiments, no MALDI signal is obtainable with traditional surfactants or surfactants (non-cleaved) of the present invention; thus, "significant" does not represent a high barrier in certain embodiments.)

In certain embodiments, the hydrophobic tail is an aromatic. In certain preferred embodiments, the hydrophobic group is an aliphatic group with 2-20 carbons. In certain, highly preferred embodiments, the hydrophobic group is an aliphatic group with 4 to 8 carbons. In certain, preferred, the hydrophobic group is an aliphatic group with 2, 3, 4, 5, 6, 7, 8, 9, 10, 11, 12, 13, 14, 15, 16, 17, 18, 19, or 20 carbons.

7.0 General Structure of Cleavable Compounds of the Present Invention

The cleavable detergents/surfactants of the present invention include those of the following basic formula:

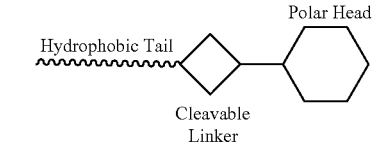

In preferred embodiments, the hydrophobic tail may comprise alkyl, alkenyl, alkynyl groups containing 2-20 carbons. Preferably these groups comprise straight chain or branched hydrocarbons, and/or single or multiple chain hydrocarbons. Preferably, the length is 4-12 carbons. Most preferably, the carbon chains have 6 or about 6 carbon atoms.

The cleavable linker may be acid cleavable. Preferred acid cleavable linkers include acetal/ketal linkers such as:

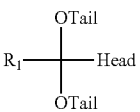 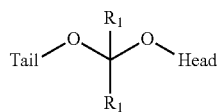

where $R_1$ is independently —H or —$(CH_2)_{0-19}CH_3$.

The cleavable linker may also be fluoride cleavable. Fluoride-cleavable linkers may include:

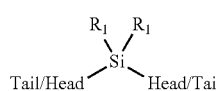

$R_1$ is independently —$CH_3$,

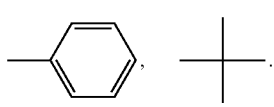

The cleavable linker may also be a disulfide/thioester such as:

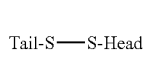  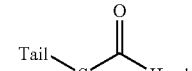

Furthermore, the cleavable linker may also be photocleavable. An example of a photocleavable linker of the present invention includes:

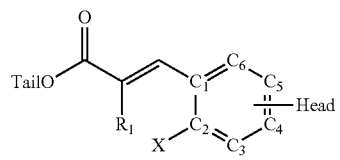

X is a group $NH_2$ or OH. $R_1$ is —H, —$CH_3$, —F, —Cl, —Br, —I, or, —CN. Head groups are attached independently on each of C4, C5, and C6.

The polar head may be the polar head in conventional cleavable detergents/surfactants, including cationic, anionic, Zwitterionic, non-ionic carbohydrates, and MALDI matrices. Examples include the following:

Cationic

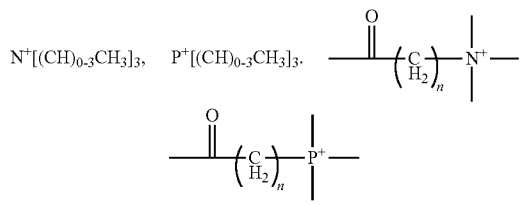

Anionic

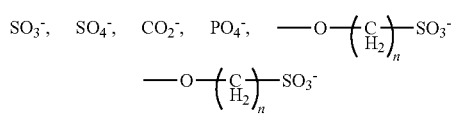

Zwitterionic

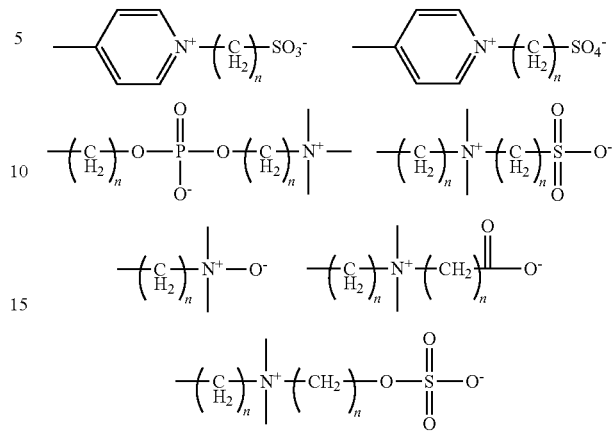

(In all the above polar head groups, n is an integer from 1-12, preferably from 1-6.)

Amino Acids, including:

Cystine

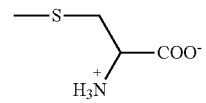

Including cystine containing peptides. (6 amino acids or less).

Non-Ionic Carbohydrates, including:

furanose

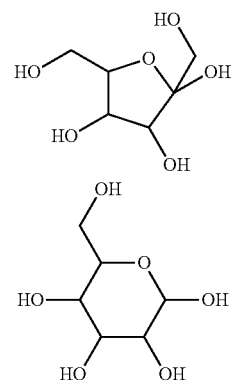

Pyranose

Including polysaccharides. (3 carbohydrates or less).

Polyethylene Glycol

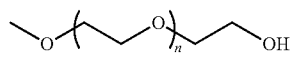

n is an integer from 1 to 20.

MALDI Matrices, including:
Sinapinic Acid

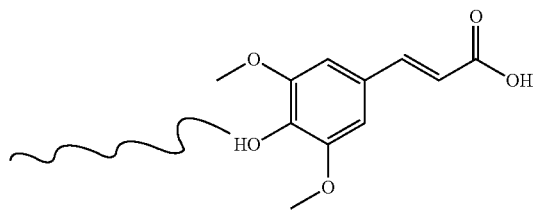 [SMILES: COc1cc(/C=C/C(=O)O)cc(OC)c1O]

α-cyano-4-hydroxycinnamic acid

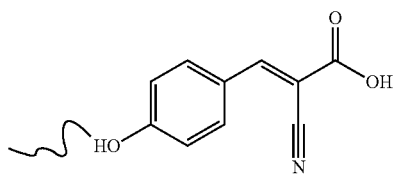 [SMILES: N#C/C(=C\c1ccc(O)cc1)C(=O)O]

2,5-Dihydroxybenzoic Acid; 3,5-Dihydroxybenzoic Acid

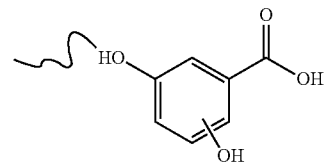

In other preferred embodiments of the present invention, the cleavable compounds of the present invention may have more than one cleavable linker, and include compounds of the following general formula:

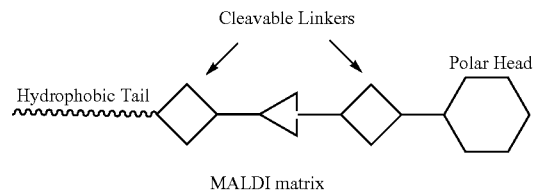

In this embodiment, the linkers, tails, and polar heads described above may be used. Additionally, it is preferred that the MALDI matrix is based on the following compounds:

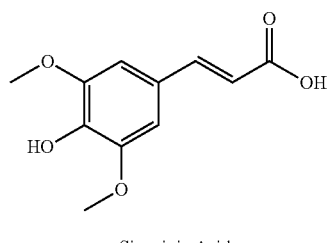

--Sinapinic Acid

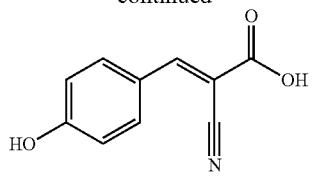

--α-cyano-4-hydroxycinnamic acid

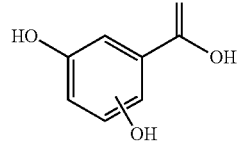

--2,5-Dihydroxybenzoic Acid; 3,5-Dihydroxybenzoic Acid 8.0 Isolation of Hydrophobic Proteins/Polypeptides In certain embodiments, membrane bound proteins are liberated from a sample of cells (cultured or collected tissue), extracted or isolated using standard procedures except that the surfactant utilized is a cleavable surfactant, preferably one described herein and more preferably a matrix cleavable surfactant. The cleavable surfactant is cleaved (e.g., by acid) and the sample is analyzed by MALDI MS.

In certain embodiments, membrane bound proteins are liberated from a sample of cells (cultured or collected tissue), extracted or isolated using standard procedures including that a standard surfactant is utilized (e.g., SDS or triton X). The standard surfactant is exchanged with one of the present invention (e.g., by dialysis exchange) and the sample is collected. The cleavable surfactant is cleaved (e.g., by acid) and the sample is analyzed by MALDI MS.

9.0 MALDI MS Analysis of Tissue Sections

In certain embodiments, a tissue section is obtained. The section is treated with a cleavable surfactant, preferably one described herein and more preferably a matrix cleavable surfactant. The section is incubated to allow certain of the proteins and other hydrophobic molecules to become solubilized by the cleavable surfactant. The cleavable surfactant is cleaved (e.g., by acid or reducing agent) and the tissue section is analyzed by MALDI MS. In an additional embodiment of the present invention, compounds of the present invention may be used in one dimensional and two dimensional polyacrylamide gel electrophoresis. Two dimensional polyacrylamide gel electrophoresis (2D-PAGE) is a technique commonly used for the analysis of mixtures of proteins. (U. K. Laemmli, Nature 227, 680-685, 1970). Proteins are separated first by an electrophoretic such as isoelectric focusing followed by a second dimension separation based on protein size. Sodium dodecyl sulfate, the detergent most often used with 2D-PAGE, forms stable non-covalent complexes with proteins. The SDS complexed proteins have identical charge density; therefore, they separate in an electrical field according to their size. This technique is capable of separating a complex protein mixture into several hundred individual components that can be excised from the gel and further identified by other techniques. One such technique is mass spectrometry. The direct analysis of proteins removed from electrophoresis gels is often difficult. Commonly, the samples contain detergent concentrations that hinder analysis by mass spectrometry. The direct analysis of proteins removed from electrophoresis gels is often difficult. Commonly, the samples contain detergent concentrations that hinder analysis by mass spectrometry. In MALDI analysis for example, this problem is the result of the tendency of the detergent to aggregate or associate with the protein preventing proper incorporation into the matrix crystal. Special steps must be taken to remove the interference prior to analysis by MALDI MS. Examples of such measures include, but are not limited to electroblotting of PAGE gels and detergent exchange of SDS with a more MALDI tolerant detergent like n-octyl-glucoside, for example.

An alternative approach is to use cleavable analogs to commonly used detergents in SDS-PAGE. For example, anionic analogs to SDS of the present invention such as the following:

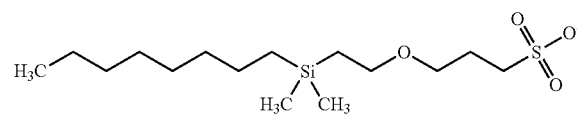

Detergents of the present invention that may be used include any cationic or anionic cleavable detergent. Preferably, anionic cleavable detergents are used.

Zwitterionic or non-ionic detergents of the present invention may be used for simple 1D gel electrophoresis in which proteins are separated based on isoelectric point. Example of preferred embodiments include the following:

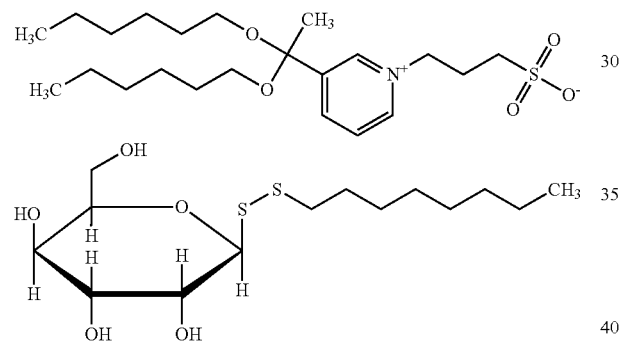

These compounds are applied according to established protocols in the analysis of proteins by gel electrophoresis. Subsequent analysis of the separated biomolecules is accomplished by excising the proteins from the gel, reconstituting the protein, and applying the sample to a MALDI target. The appropriate cleavage agent is applied to the sample along with the matrix, if necessary, allowing more accurate mass spectrometry determination of molecular weight. With respect to electrophoresis of proteins, see Westermeier, Electrophoresis in paractice, 3rd Edition, 2001; and Flames, Gel electrophoresis of proteins: a practical approach, 3rd Edition, 1998.

The following examples are for illustrative purposes, and not intended to limit the scope of the invention as defined by the claims. Additionally, in practicing the present invention, one of ordinary skill in the art would understand that various modifications to the following procedures would be routine, in light of the teachings herein, and that such modifications would be within the spirit and scope of the present invention.

EXAMPLES

Example 1

Example 1 is a selection of embodiments of cleavable detergents or surfactants of the present invention, including the hydrophobic tail, cleavable linker, and polar head group.

A composition of Formula 14:

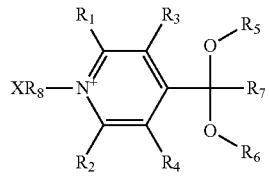

X can be $SO_3^-$, $SO_4^-$, or $N^+(OH_3)_3$
or a salt thereof, wherein:
R1 and R2 is each independently —H, -OCH$_3$, —(CH$_2$)$_{1-6}$CH$_3$, or -O(CH$_2$)$_{1-6}$CH$_3$;
R3 and R4 is each independently —H, -OCH$_3$, —OH, —NH$_2$, —(CH$_2$)$_{1-6}$CH3, or -O(CH$_2$)$_{1-6}$CH$_3$;
R5 and R6 are each independently —(CH$_2$)$_{1-19}$CH$_3$;
R7 is independently —(CH$_2$)$_{1-19}$CH$_3$; and
R8 is independently —(CH$_2$)$_{1-6}$,
X is independently $SO_3^-$, $SO_4^-$, or $NH_3^+$.

A preferred embodiment of formula 14 is where that R1 and R4 are H, and R7 is methyl. The basic structure defined by R5—O—C—O—R6 is that of a ketal linkage. The present set of structures is especially useful for the ability to degrade the surfactant by cleavage at the ketal yielding molecules with reduced MALDI signal suppression.

Compositions of Formula 15:

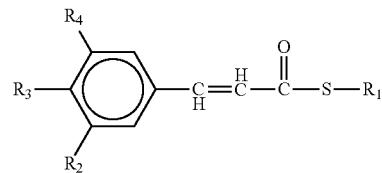

or a salt thereof, wherein:
R1 is independently an aromatic or —(CH$_2$)$_{1-19}$CH$_3$;
R2, R3, R4 is each independently —H, -OCH$_3$, —(CH$_2$)$_{1-6}$CH$_3$, or -O(CH$_2$)$_{1-6}$CH$_3$;
Compositions of Formula 16:

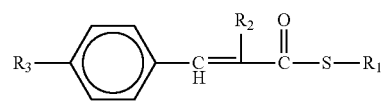

R2 is Cyano, Halide, or methyl or H
or a salt thereof, wherein:
R1 is independently an aromatic or —(CH$_2$)$_{1-19}$CH$_3$;
R2 is —H, methyl, halide, halogen, or cyano (—CN); and
R3 independently —H, —OH, -OCH$_3$, —(CH$_2$)$_{1-6}$CH$_3$, or -O(CH$_2$)$_{1-6}$CH$_3$;
Compositions of Formula 17:

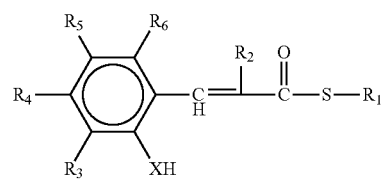

R2 is Cyano, Halide, or methyl, or H or a salt thereof, wherein:

R1 is independently an aromatic or —(CH$_2$)$_{1-19}$CH$_3$;

R2 is —H, methyl, halide, or cyano (—CN);

R3, R4, R5, and R6 is each independently —H, -OCH$_3$, —(CH$_2$)$_{1-6}$CH$_3$, or -0(CH$_2$)$_{1-6}$CH$_3$; and X is oxygen, —NH, or a nucleophile.

Compositions of Formula 18:

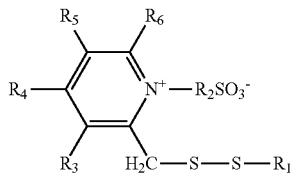

or a salt thereof, wherein:

R1 is independently an aromatic or —(CH$_2$)$_{1-19}$CH$_3$;

R2 is independently —(CH$_2$)$_{1-6}$; and

R3, R4, R5, and R6 is each independently —H, -OCH$_3$, —(CH$_2$)$_{1-6}$CH$_3$, or -0(CH$_2$)$_{1-6}$CH$_3$. Additionally, the chain with R1 and R4 are substituted one for the other.

Compositions of Formula 19:

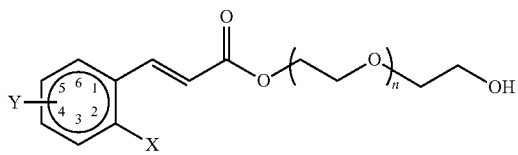

or a salt thereof, wherein:

n is an integer of from 1 to 20;

Y is independently positioned at one or more of C3, C4, C5, or C6, wherein Y represents independently —H, or a straight or branched chain, substituted or unsubstituted: alkyl, alkene, and alkyne; and X is oxygen, —NH, or a nucleophile.

Included in this Example are the following formulas:

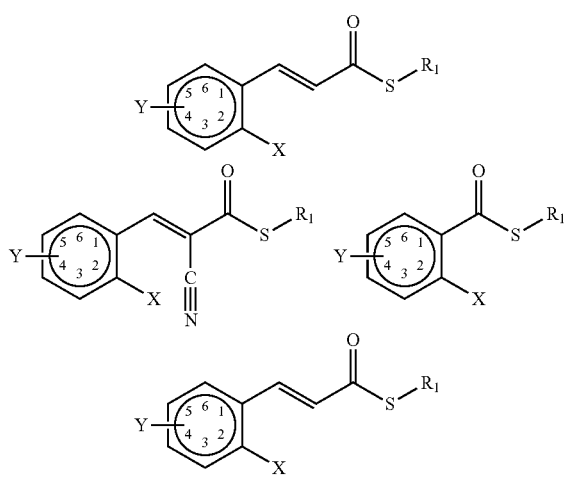

or a salt thereof, wherein:

R1 is independently an aromatic or —(CH$_2$)$_{1-19}$CH$_3$;

Y is independently positioned at one or more of C3, C4, C5, or C6, wherein Y represents independently —H, -OCH$_3$, —(CH$_2$)$_{1-6}$CH$_3$, or -0(CH$_2$)$_{1-6}$CH$_3$; and X is oxygen, —NH, or a nucleophile.

Also included in this Example are the following formulas:

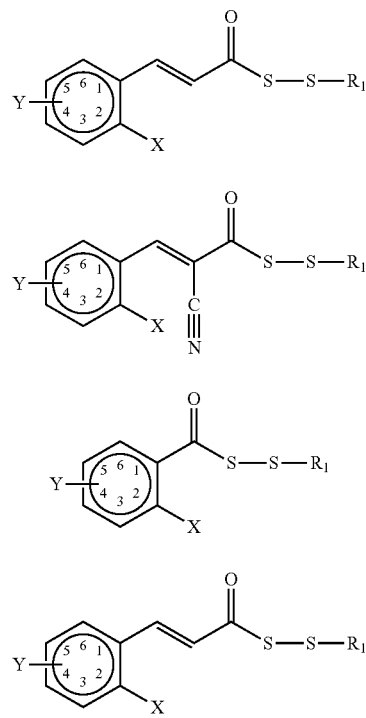

or a salt thereof, wherein:

R1 is independently an aromatic or —(CH$_2$)$_{1-19}$CH$_3$;

Y is independently positioned at one or more of C3, C4, C5, or C6, wherein Y represents independently —H, -OCH$_3$, —(CH$_2$)$_{1-6}$CH$_3$, or -0(CH$_2$)$_{1-6}$CH$_3$; and X is oxygen, —NH, or a nucleophile.

Also included in this Example are the following formulas:

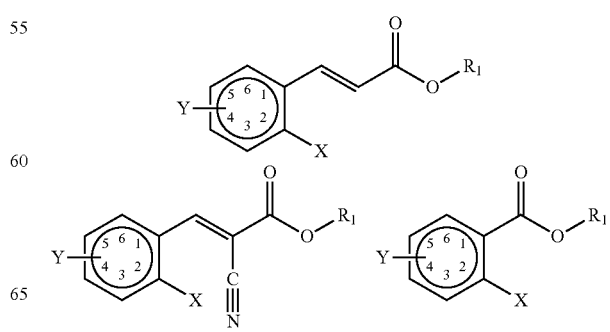

-continued

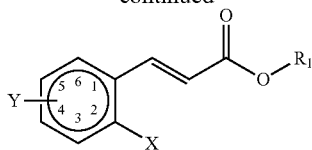

or a salt thereof, wherein:
R1 is independently an aromatic or —$(CH_2)_{1-19}CH_3$;
Y is independently positioned at one or more of C3, C4, C5, or C6, wherein Y represents independently —H, -$OCH_3$, —$(CH_2)_{1-6}CH_3$, or -$O(CH_2)_{1-6}CH_3$; and
X is oxygen, —NH, or a nucleophile.

Finally, also included in this Example are the following formulas:

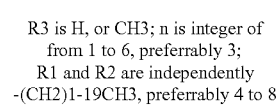 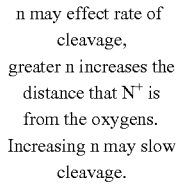

R3 is H, or CH3; n is integer of from 1 to 6, preferably 3;
R1 and R2 are independently -(CH2)1-19CH3, preferably 4 to 8 n may effect rate of cleavage, greater n increases the distance that $N^+$ is from the oxygens. Increasing n may slow cleavage.

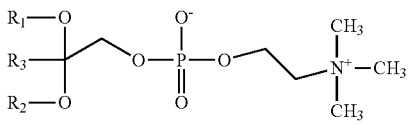

R3 is H or CH3; n is integer of from 1 to 6, preferably 3;
R1 and R2 are independently -(CH2)1-19CH3, preferably 4 to 8

Example 2

This Example describes the synthesis and cleavage of alpha-cyano-4-hydroxy-cinnamic acid detergent, a preferred embodiment of the present invention.

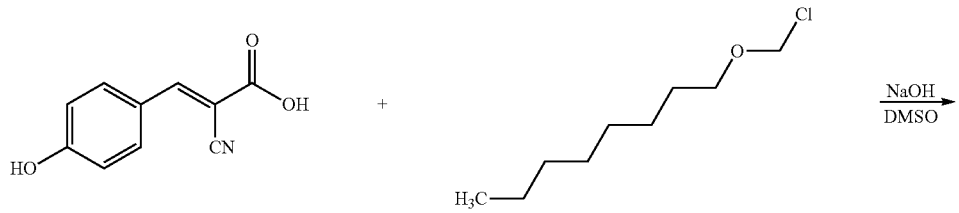

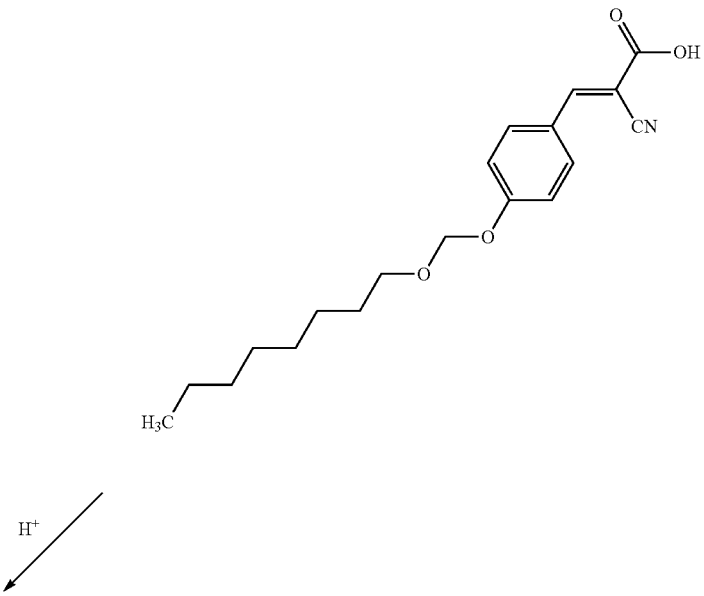

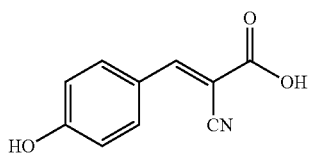

Synthesis of Chloromethyl ether: A volume of 5 mL (39.4 mmol) of chlorotrimethylsilane (TMS-Cl) and 0.3 g of paraformaldehyde were placed in a flame dried 25 mL round bottom flask. The reagents are allowed to stir under inert atmosphere until homogeneous. A volume of 2.27 mL (10 mmol) of n-dodecanol were added drop wise to the reaction vessel. The reagents react at room temperature for a period of two hours. The TMS-Cl is removed under vacuum followed by a vacuum distillation of the product, chloromethyl ether. A total of 0.973 g (41% yield) of product were collected at 106°-109° C. at 0.4 torr.

Synthesis of the methoxyalkyl ether of α-cyano-4-hydroxycinnamic acid

Powdered NaOH (107 mg, 2.68 mmol) was dissolved in 2 mL of dimethylsulfoxide in a flame dried 25 mL round bottom flask. To this mixture, 0.302 g (1.35 mmol) of α-cyano-4-hydroxycinnamic acid was added to the reaction. The reaction mixture was placed under inert atmosphere and allowed to stir until all reagents were dissolved.

At this time, 0.255 g (1.08 mmol) of the newly synthesized chloromethyl ether was added drop wise to the reaction mixture. The reaction was allowed to stir for a period of 12-16 hours. TLC confirmed that the reaction was complete. Reaction mixture was diluted with chloroform and washed repeatedly with saturated NaCl. Remaining traces of DMSO were removed under vacuum with an in-line cold trap. A weight of 0.653 g (65.3% yield) of product was purified.

Example 3

This Example describes the synthesis and cleavage of sinapinic acid detergent, a preferred embodiment of the present invention.

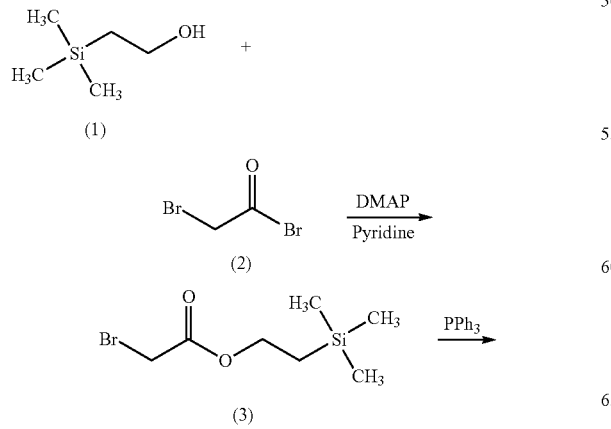

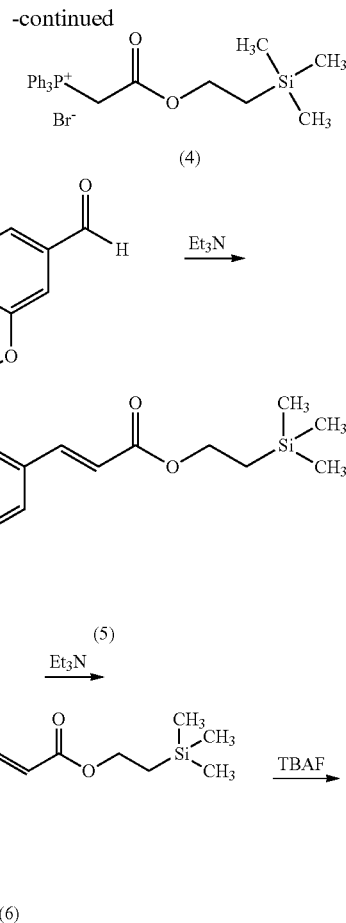

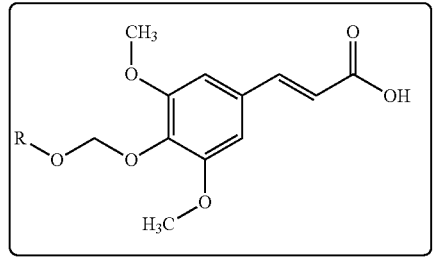

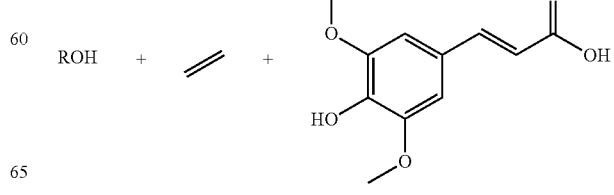

Synthesis of Chloromethyl ether

A volume of 5 mL (39.4 mmol) of chlorotrimethylsilane (TMS-Cl) and 0.3 g of paraformaldehyde were placed in a flame dried 25 mL round bottom flask. The reagents are allowed to stir under inert atmosphere until homogeneous. A volume of 2.27 mL (10 mmol) of n-dodecanol were added drop wise to the reaction vessel. The reagents react at room temperature for a period of two hours. The TMS-Cl is removed under vacuum followed by a vacuum distillation of the product, chloromethyl ether. A total of 0.973 g (41% yield) of product were collected at 106°-109° C. at 0.4 torr.

Synthesis of protected sinapinic acid (5)

Synthesis of trimethylsilylethyl bromoacetate (3): In a dry 50 mL round bottom flask, 1.65 mL (11.54 mmol) of trimethylsilyl ethanol (1), 0.88 mL (11 mmol) of pyridine, 0.124 g (1 mmol) of N,N-dimethylaminopyridine, and 20 mL of methylene chloride were placed. The reaction mixture was placed under inert atmosphere. A volume of 0.97 mL bromoacetyl bromide (2) was added drop wise to the reaction mixture. The reaction proceeded for two hours at room temperature. Reaction was washed twice with 1 M HCl followed by a wash with saturated NaCl. The organic layer was dried over MgSO4. A quantitative yield was obtained, 2.74 g of trimethylsilylethyl bromoacetate (3).

Synthesis of phosphonium salt (4): To the 2.74 g (11.46 mmol) of trimethylsilylethyl bromoacetate (3) previously synthesized, 4.51 g (17.20 mmol) of triphenylphosphine and 20 mL of ethyl acetate were added. The reagents were stirred at room temperature for 24 hours. A white precipitate formed which was isolated by vacuum filtration. A mass of 4.08 g (8.14 mmol, 71.0% yield) of phosphonium salt (4) was isolated.

Synthesis of protected sinapinic acid (5): An amount of 0.824 g (1.65 mmol) of the phosphonium salt (4) previously synthesized was added to 0.23 mL (1.65 mmol) of trimethylamine in 5 mL of benzene. A yellow solution of ylide formed within 30 minutes. Syringaldehyde (0.274 g, 1.5 mmol) was added to the ylide and stirred for 16 hours. The organic layer was washed with 1 M HCl. Further purification was accomplished using flash chromatography (3:2 ethyl acetate/hexane). A yield of 73.1% (0.356 g) of protected sinapinic acid was obtained.

Synthesis of the methoxyalkyl ether of sinapinic acid

In a dry round bottom flask, 0.2 mL (1.43 mmol) of trimethylamine, 0.308 g (0.951 mmol) of protected sinapinic acid (5) and 0.271 g (0.836 mmol) of the newly synthesized chloromethyl ether were added placed. The reaction was stirred for 12 hours at room temperature. Product 6 was purified using alumina flash chromatography with methylene chloride as the mobile phase. An amount of 0.402 g (0.770 mmol, 92.1% yield) of compound 6 was isolated.

Deprotection

To 0.402 g (0.770 mmol) of compound 6 in 2 mL of tetrahydrofuran, 0.65 g of tetrabutylammonium fluoride was added. An immediate yellow color was observed. The reaction proceeded at room temperature for one hour. The product was extracted from saturated ammonium chloride with methylene chloride. An amount of 0.320 g (0.762 mmol, 99.0% yield) of deprotected sinapinic acid detergent was obtained.

Example 4

This Example describes the systhesis of dihydroxybenzoic acid detergent, and acid and/or fluoride cleavage.

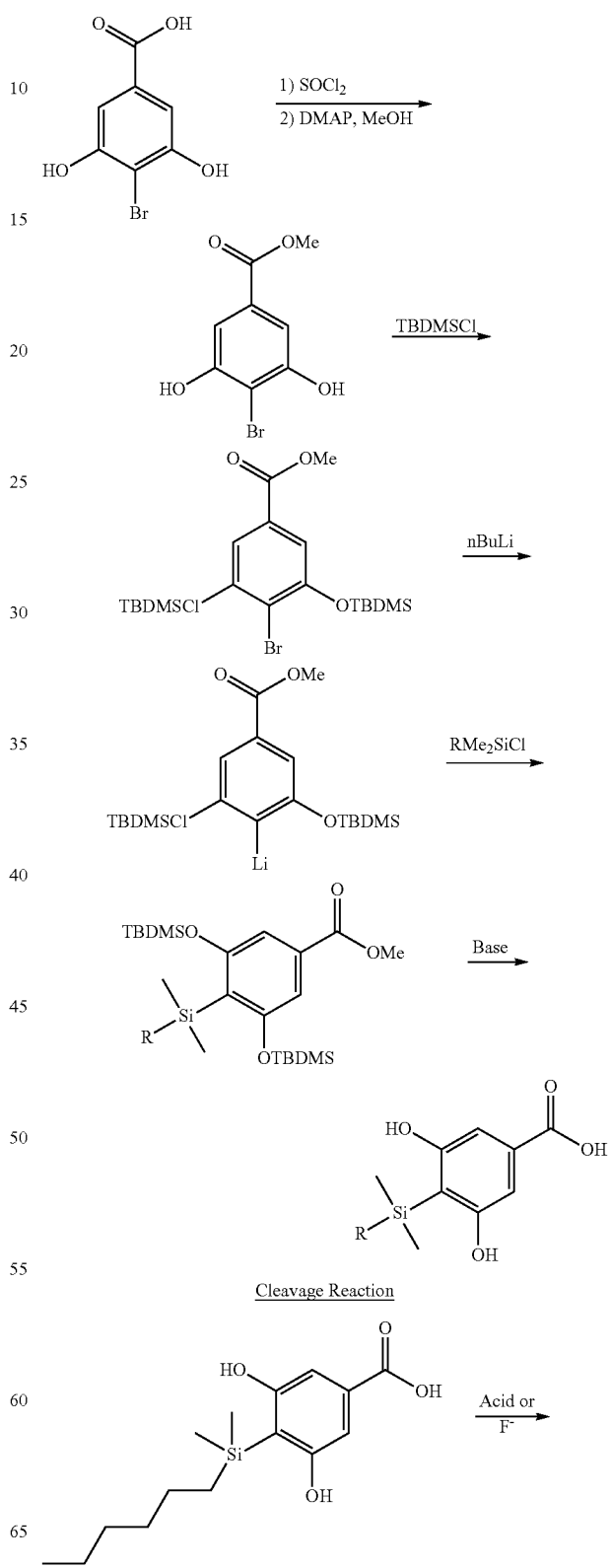

27
-continued
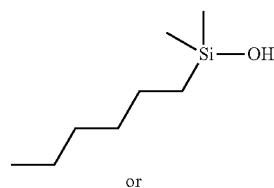
or
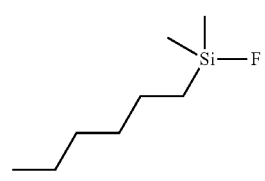
28
-continued
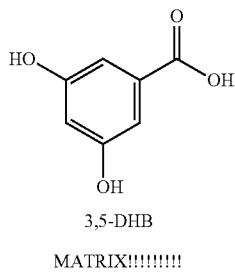
3,5-DHB
MATRIX!!!!!!!!!
Example 5
This Example describes the synthesis and cleavage of disulfide detergent, a preferred embodiment of the present invention.
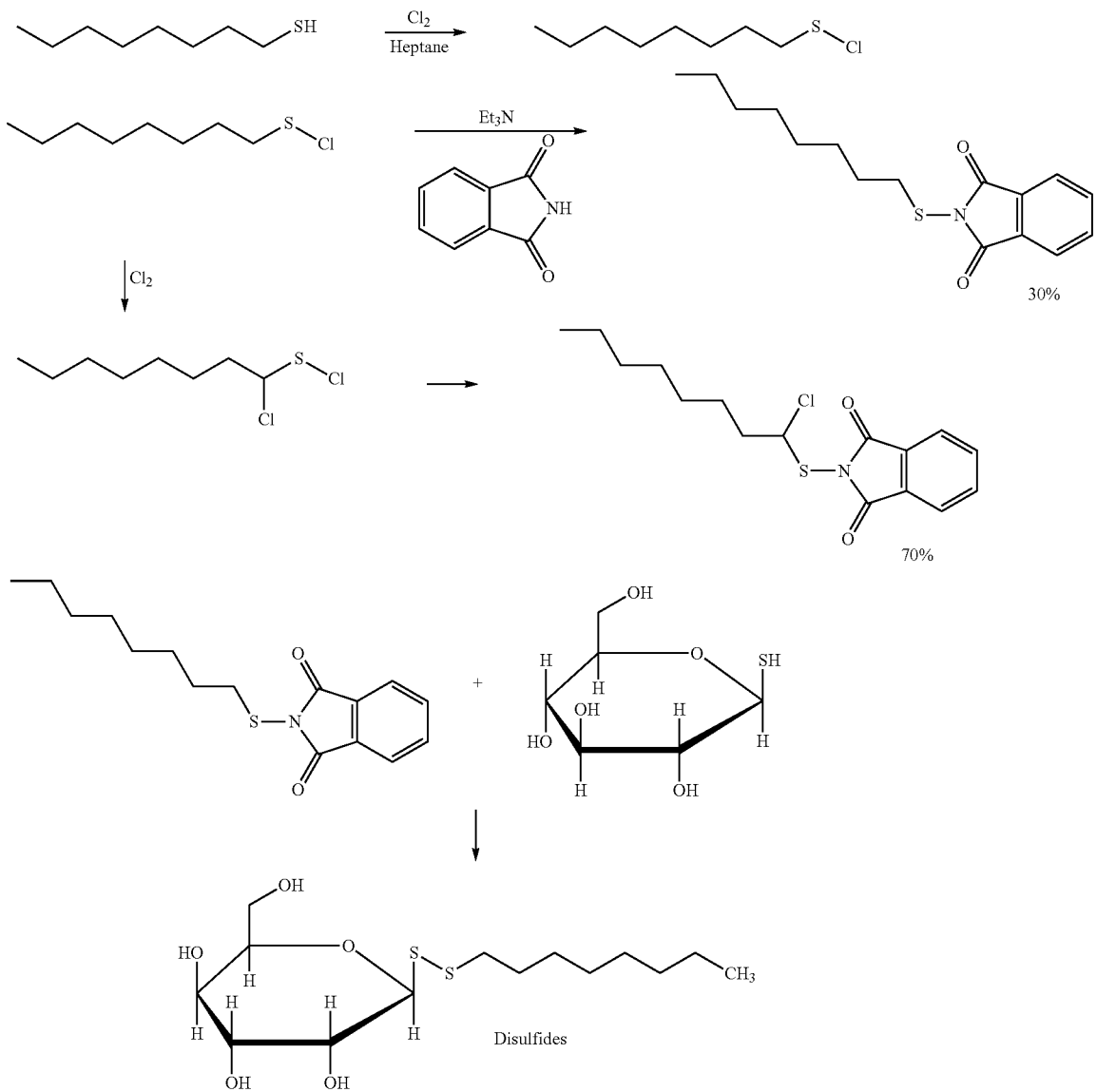

Octylthiophthalimide was prepared according to behforouz et al.: a volume of 10 ml (57.62 mmol) of octane thiol were placed in a 250 ml round bottom flask with 75 ml of heptane. Chlorine gas was bubbled through the solution. Conversion of octane thiol to the corresponding sulfenyl chloride, as monitored using gas chromatography, occurred in approximately 30 minutes. Drop wise addition of 8.5 g (57.8 mmol) of phthalimide and 8 ml (57.5 mmol) of trimethylamine in 75 ml of n,n-dimethylformamide converted the sulfenyl chloride to octylthiophthalimide. After stirring 30 minutes, the reaction was added to 100 ml of cold water, then the precipitant was collected by filtration. The product was further purified using column chromatography (1:2 ethyl acetate/hexanes). yields greater than 95% conversion of octane thiol were obtained.

Synthesis of glucose based non-ionic disulfide detergent according to Harpp et al.: Equimolar amounts of 1-thio-β-D-glucose and octylthiophthalimide were refluxed in ethanol for 12 to 20 hours. Formation of the unsymmetrical disulfide proceeded with greater than 80% yield.

Example 6

This Example describes fluoride cleavable detergents of the present invention.

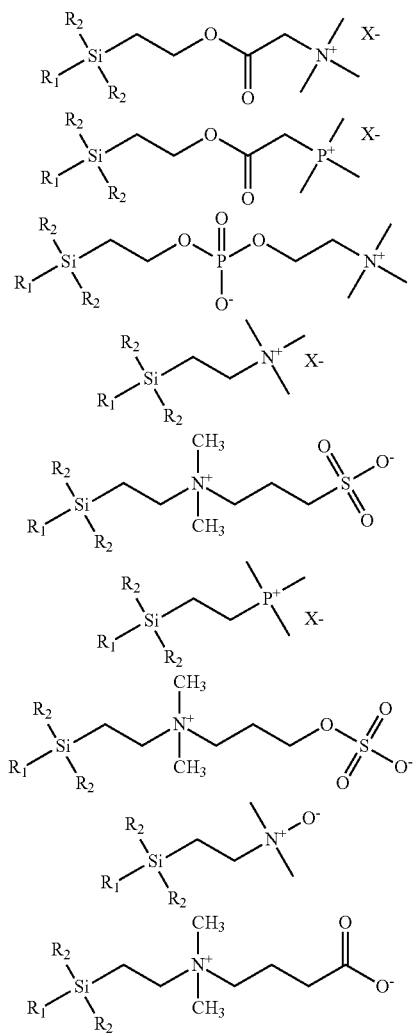

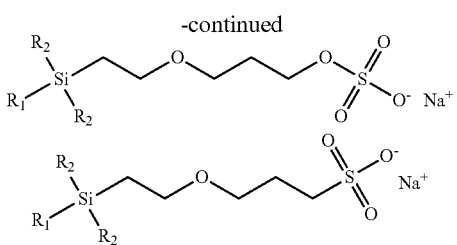

$R_1$=Alkyl, Alkenyl, Alkynyl (C4-C20).
$R_2$=-Me, -tBu, -φ.
X=Cl, Br, I

Example 7

This Example describes synthesis of fluoride clevable analogs of CTAB.

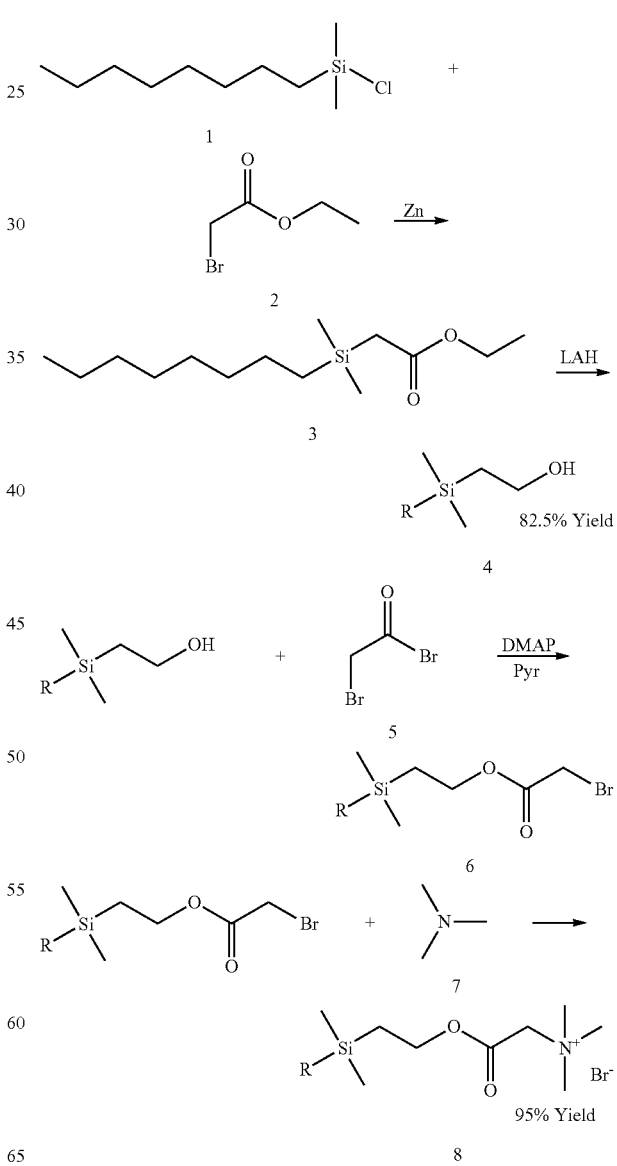

78% Overall Yield
CMC=1.685 (Dye Solubilization)

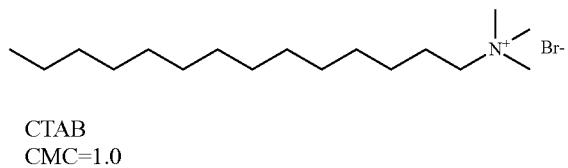

CTAB
CMC=1.0

Synthesis of ethyl alkyldimethylsilylacetate (3)

All reagents were purified prior to use. A dry 250 mL flask was fitted with a condenser and an addition funnel. An amount of 2.03 g (31.0 mmol) of powdered zinc was placed into the flask under inert atmosphere. To a mixture of 65 mL benzene and 15 mL diethyl ether, 3.46 g (16.77 mmol) of chlorodimethloctyl silane (1) and 2.4 mL (21.6 mmol) of ethyl bromoacetate (2) were added and the reagents were placed in the dropping funnel. Approximately 10 mL of the reagent mixture were added to the zinc; initiation was evident after approximately 5 minutes. The additional reagents were added drop wise over 30 minutes. The reaction was allowed to proceed for 20 hours at room temperature. The reaction was quenched using 40 mL of 1 M HCl. The organic layer was further washed with 1 M HCl, water, saturated bicarbonate, and water. The organic layer is dried over magnesium sulfate. Compound 3 was produced in 82.5% yield (3.57 g).

Synthesis of alkyldimethylsilyl ethanol (4)

An amount of 2.05 g (7.75 mmol) of compound 3 was refluxed with 0.55 g (14.3 mmol) of lithium aluminum hydride in 50 mL of ether for one hour. After cooling to room temperature, 0.55 mL of water, 0.55 mL of 15% NaOH, and 1.65 mL of water were added sequentially with stirring. The precipitates were removed by filtration through celite. The alcohol was produced at 85.7% yield (1.47 g).

Synthesis of alkyldimethylsilylethyl bromoacetate (6)

A volume of 0.658 mL (3.05 mmol) of alkyldimethylsilyl ethanol (4), 0.267 mL (3.3 mmol) of pyridine, 0.122 g (1 mmol) of N,N-dimethylaminopyridine, and 20 mL of methylene chloride were placed in a 50 mL round bottom flask. The reaction mixture was placed under inert atmosphere. A volume of 0.290 mL bromoacetyl bromide (5) was added drop wise to the reaction mixture. The reaction proceeded for two hours at room temperature. The reaction mixture was washed twice with 1 M HCl followed by a wash with saturated NaCl. The organic layer was dried over $MgSO_4$. Quantitative yield was obtained, 1.01 g of alkyldimethylsilylethyl bromoacetate (6).

Synthesis of fluoride cleavable cationic detergent (8)

Trimethyl amine (7) was condensed over 0.88 g of compound (6) in a pressure tube. Tube was sealed, and the reaction stirred overnight at room temperature. A brown precipitant formed within an hour. The tube is cooled to −78° C., opened, then the reaction is allowed to return to room temperature. When the trimethyl amine had evaporated, 0.89 g (2.24 mmol) of product (8) remained (86.1%).

Example 8

This Example describes synthesis and cleavage of fluoride cleavable detergents with matrix headgroups.

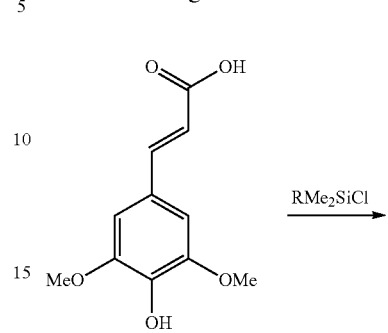

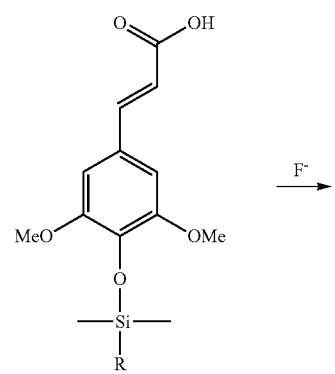

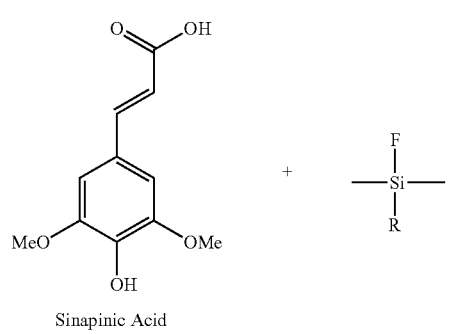

Sinapinic Acid

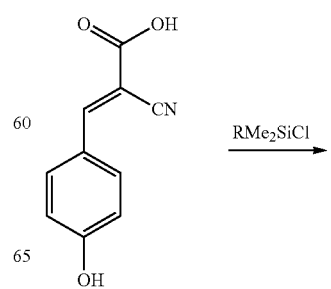

33
-continued
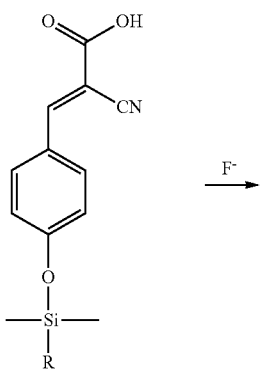
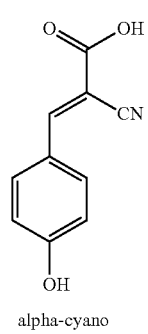
alpha-cyano
34
-continued
Other Examples:
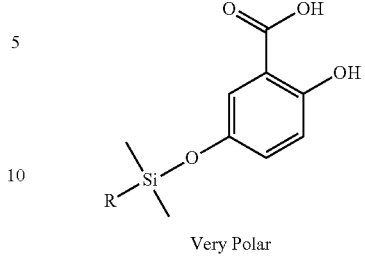
Very Polar
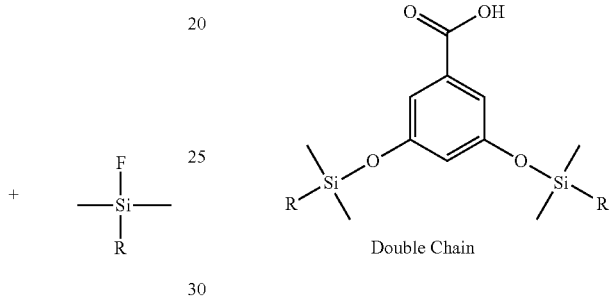
Double Chain
Example 9
This Example describes synthesis of sinapinic acid detergents that are fluoride cleavable.
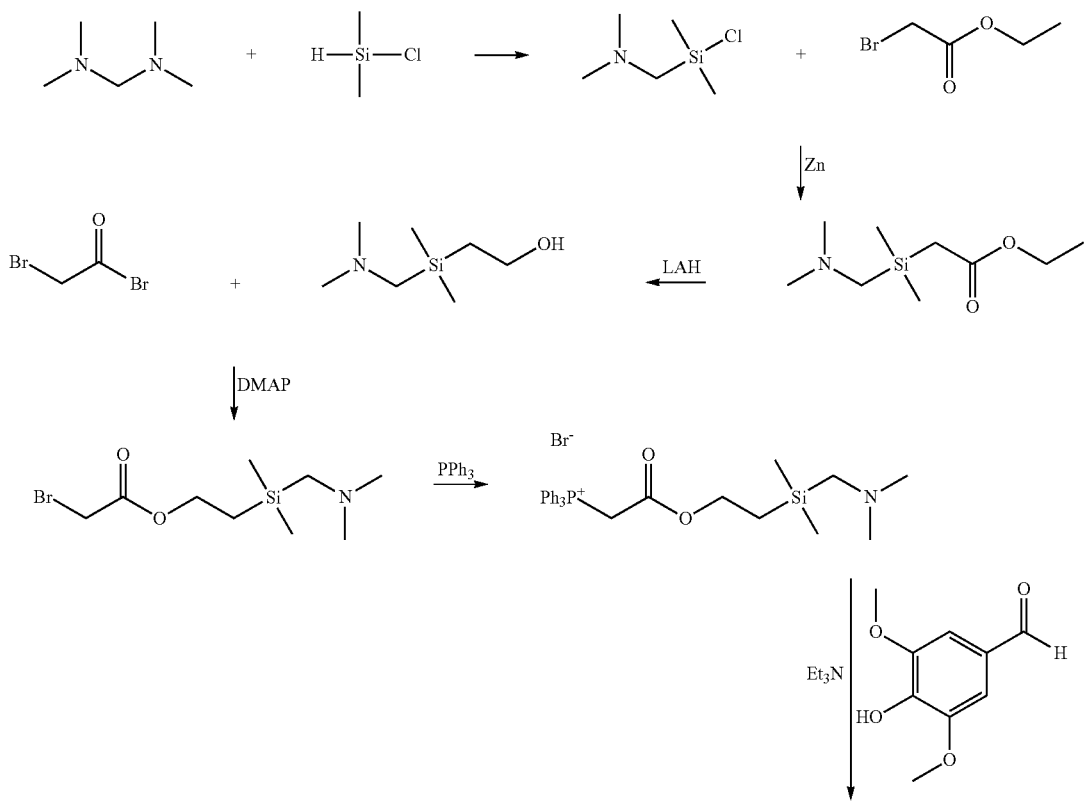

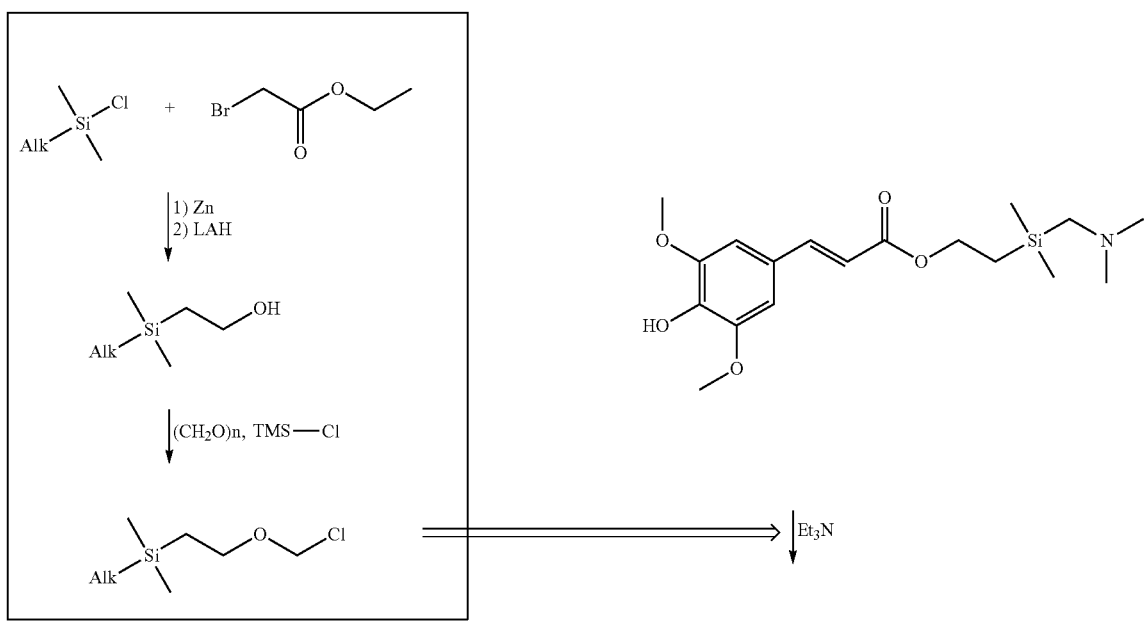
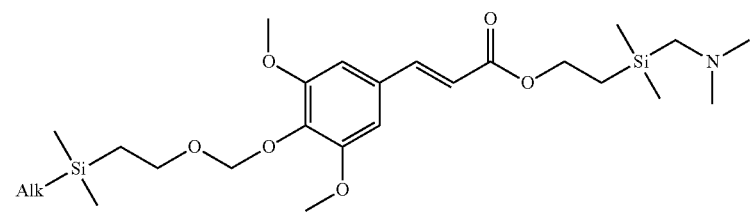
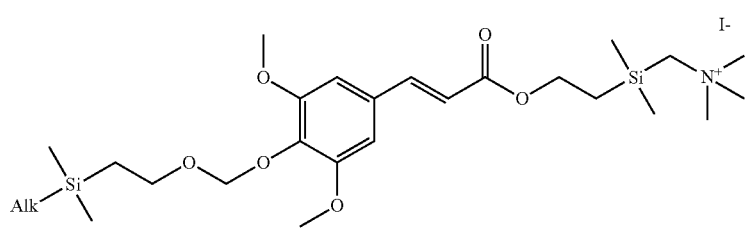

Example 10

This Example describes the synthesis and cleavage of m-PPS, a preferred embodiment of the present invention.

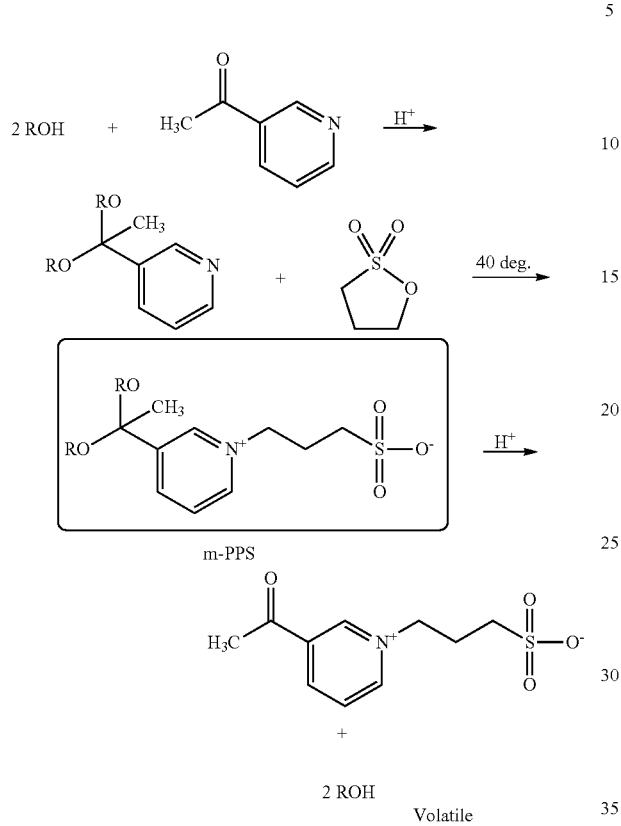

m-PPS

Figure 2:
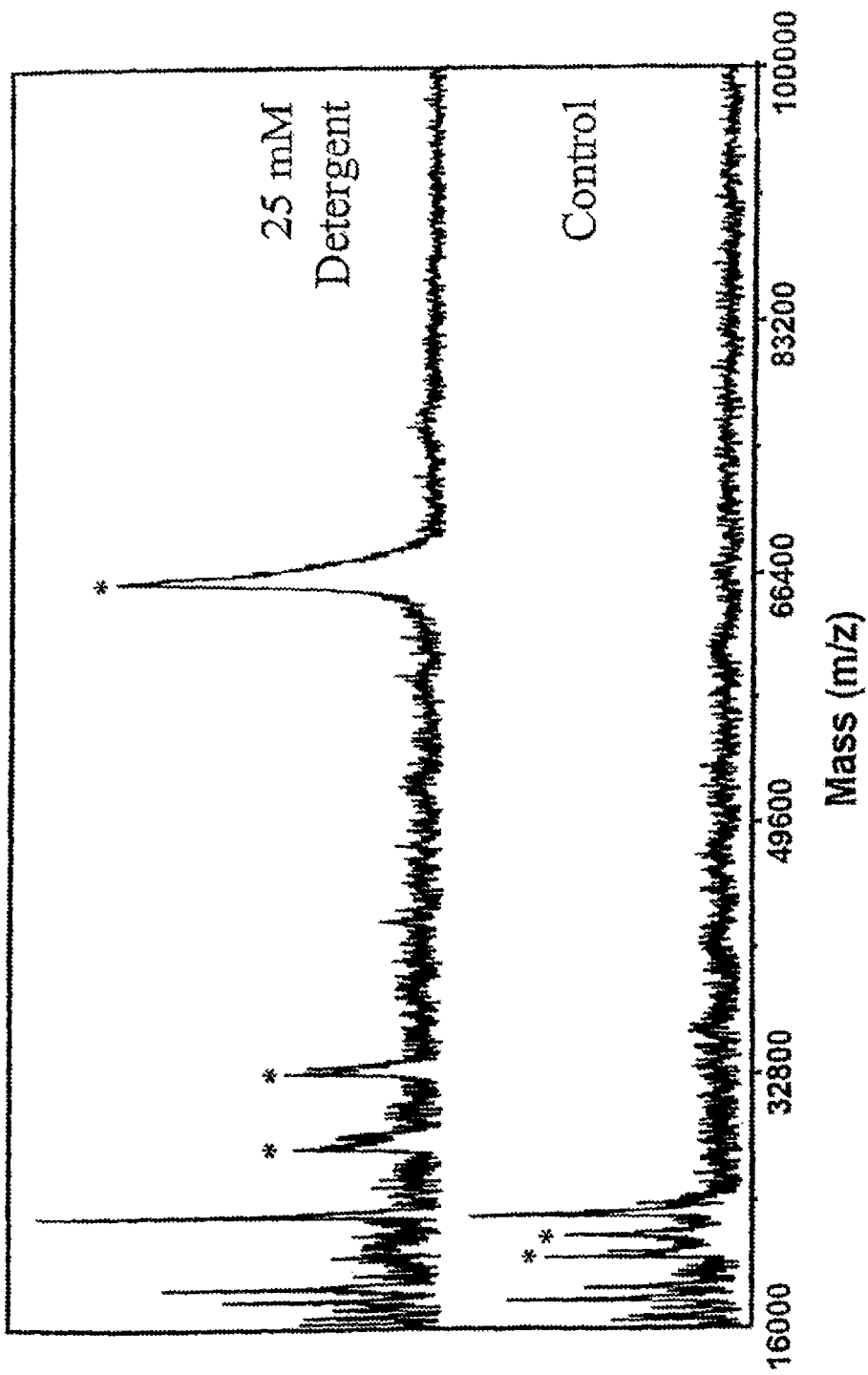
FIG. 2: a chart describing the MALDI mass spectra of a cleavable detergent of the present invention in an analysis of mouse liver extract—high mass.
Figure 3:
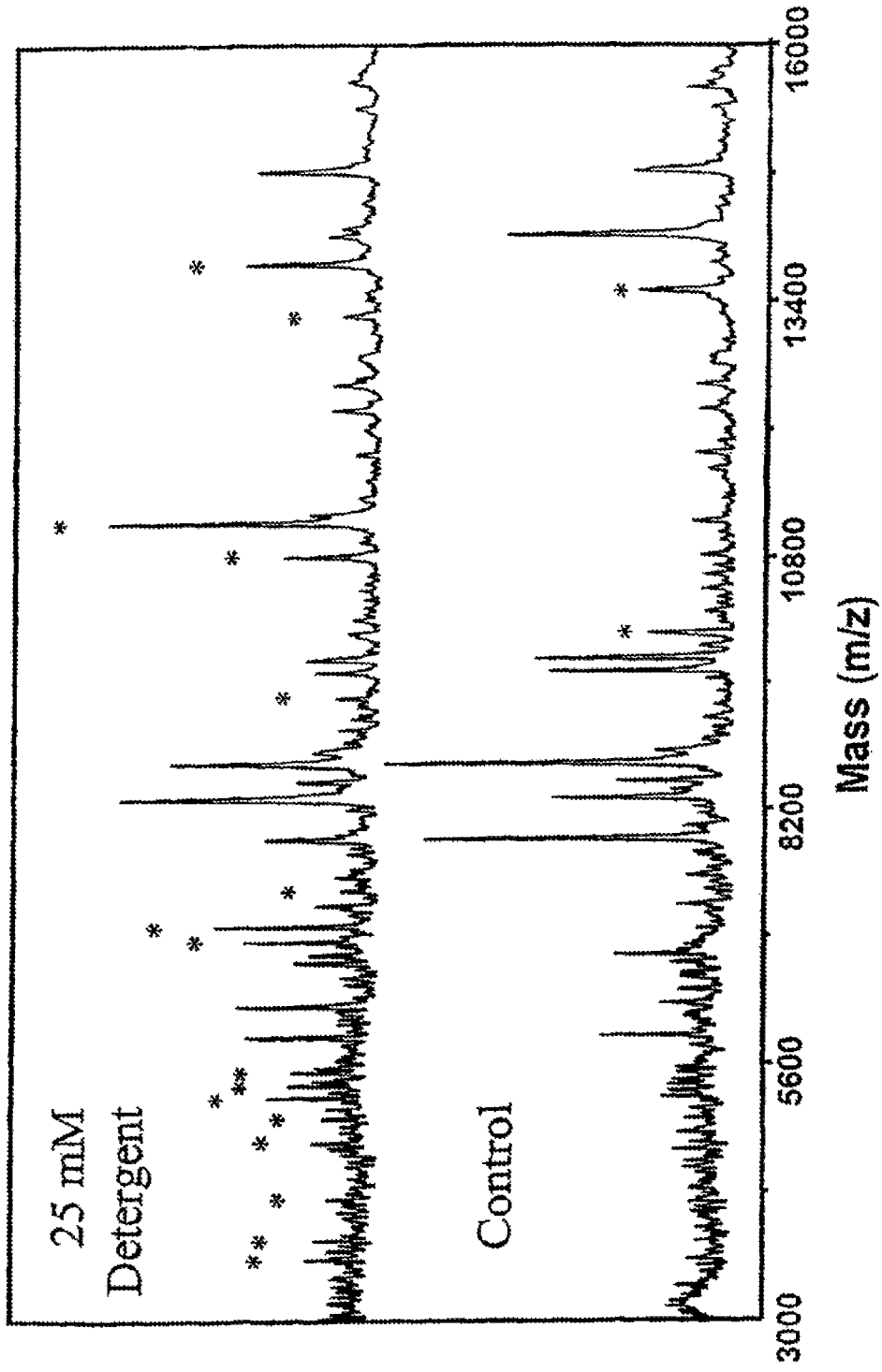
FIG. 3: a chart describing the MALDI mass spectra of a cleavable detergent of the present invention in a direct analysis of mouse liver.
Figure 4:
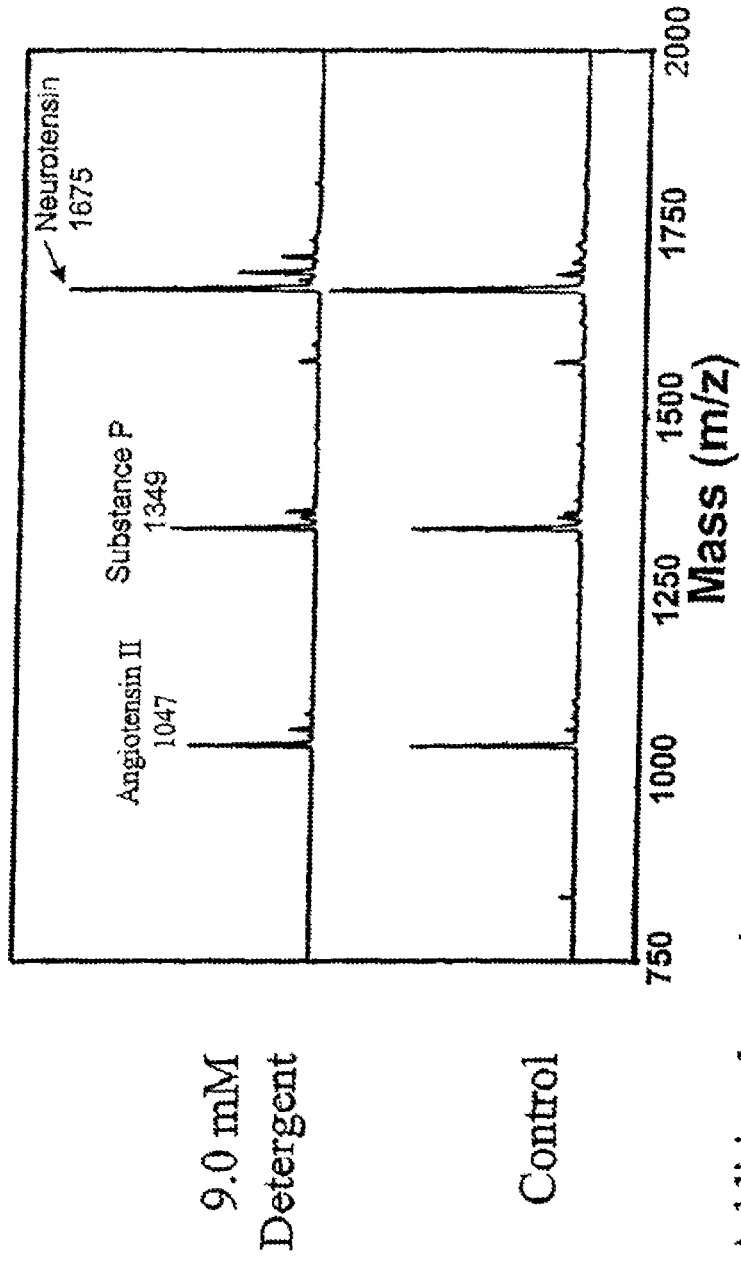
FIG. 4: a chart describing mass spectrometry analysis using an alpha-cyano detergent of the present invention.
Figure 5:
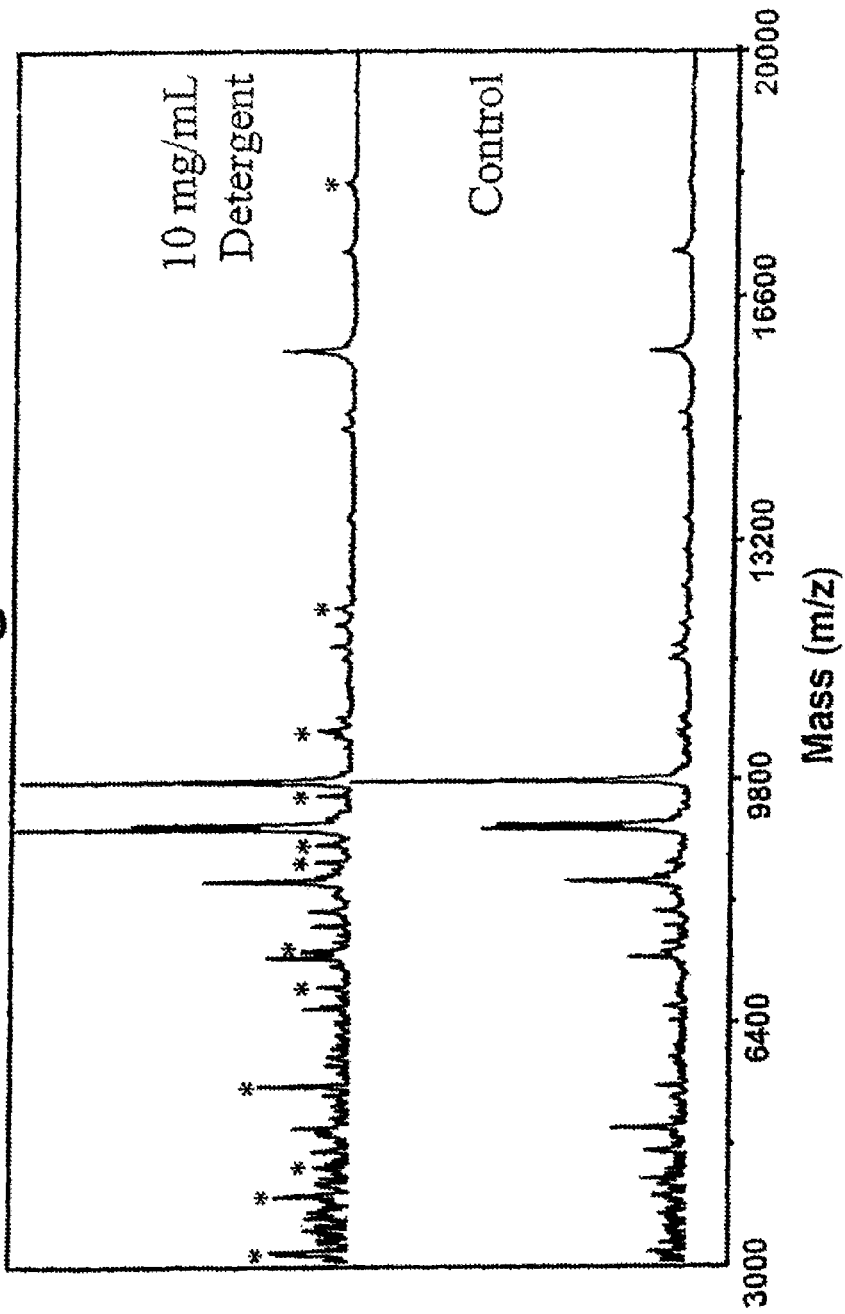
FIG. 5: a chart describing mass spectrometry analysis using an alpha-cyano detergent of the present invention treating *E. coli*.
Figure 6:
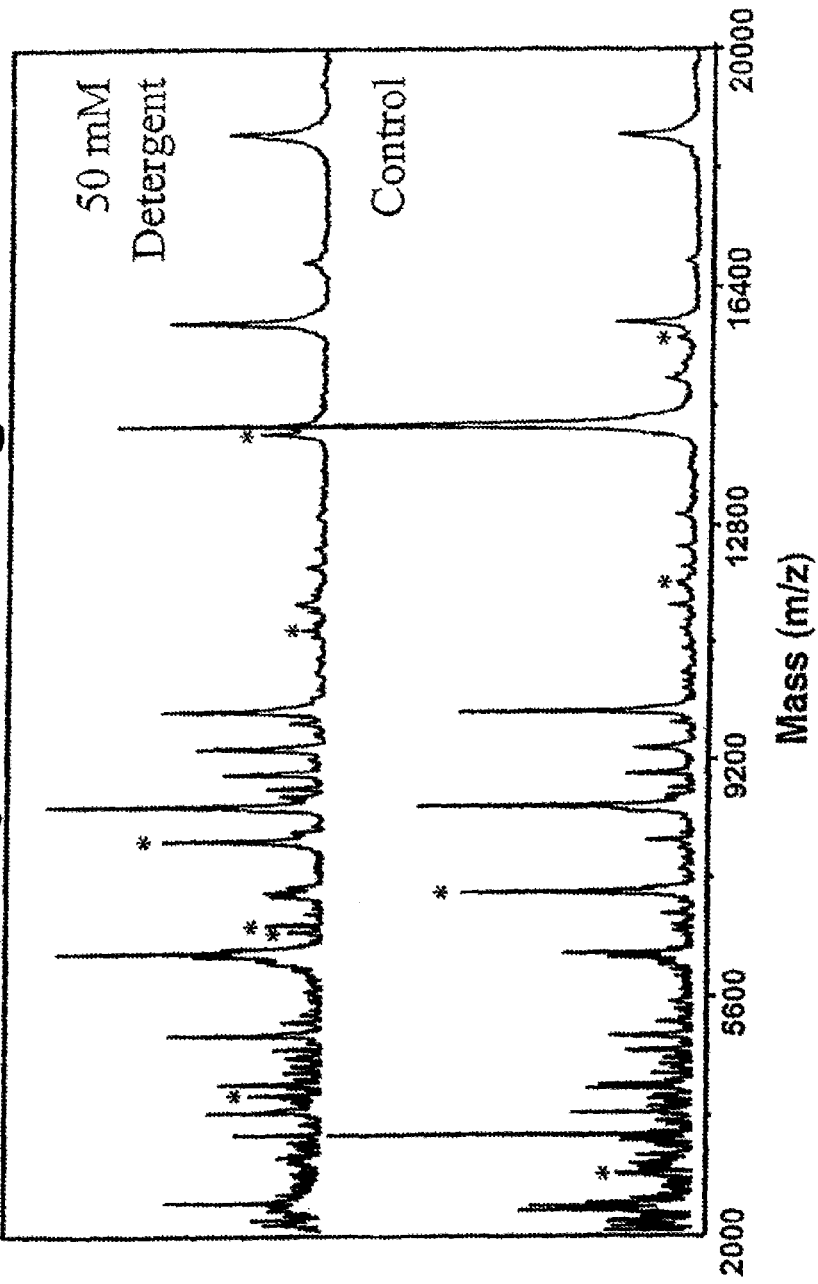
FIG. 6: a chart describing mass spectrometry analysis of mouse liver using an alpha-cyano detergent of the present invention.
Figure 7:
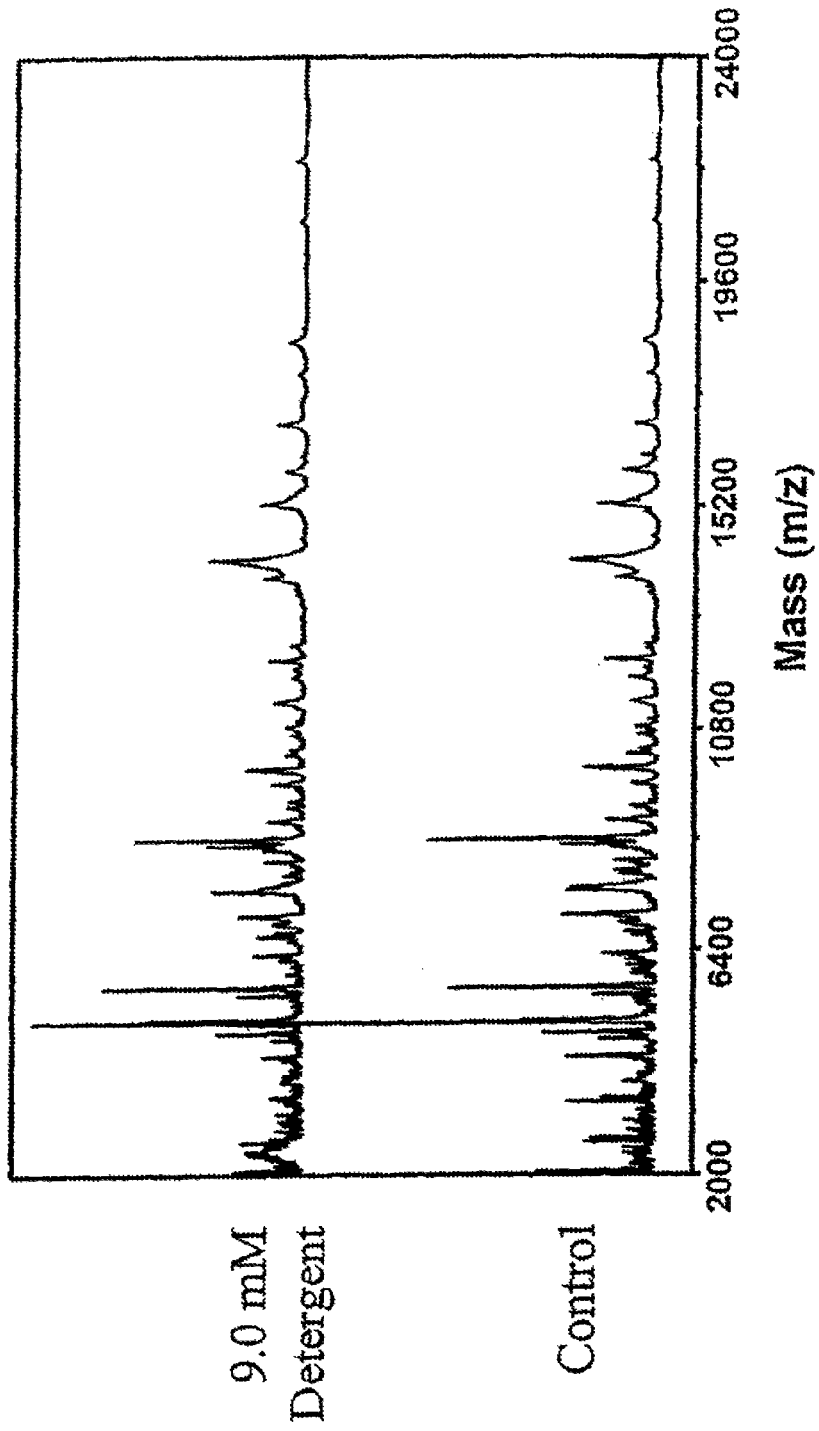
FIG. 7: a chart describing mass spectrometry analysis of direct tissue using an alpha-cyano detergent of the present invention.

FIG. 1 describes the MALDI mass spectra of a compound of this example. The solvent composition is about 25 mM in ACN/water. The ratio of tissue/solvent required is about 50 mg/mL. The concentration of acid is about 1:10 ratio of 1% HCl/detergent. The mouse liver was homogenized in the appropriate detergent solution and centrifuged for 10 min. The cleavage was initiated on plate by 0.1 uL 1% HCl to 0.5 uL drop of liver extract. 0.5 uL of sinapinic acid (10 mg/mL in 50% CAN) was added after 2-3 minutes. The graphs of FIGS. 2 and 3 were generated as part of this Example as well.

Example 11

This Example describes mass spectrometry experiments conducted according to the present invention where a solution of AC detergent was prepared in 10% acetonitrile. A standard mixture of peptides was used. Cleavage was carried out on target using 1:10 ratio of 1% HCl/detergent solution. FIGS. 4-7 were generated as part of this Example.

It would be obvious to one of ordinary skill in the art that the present invention may be practiced using equivalents of the embodiments described herein. Such equivalents are intended to be encompassed by the claims of the present invention.

All patents and publications cited herein are hereby expressly incorporated by reference in their entirety.

We claim:

1. A cleavable surfactant/detergent compound of the following formula:

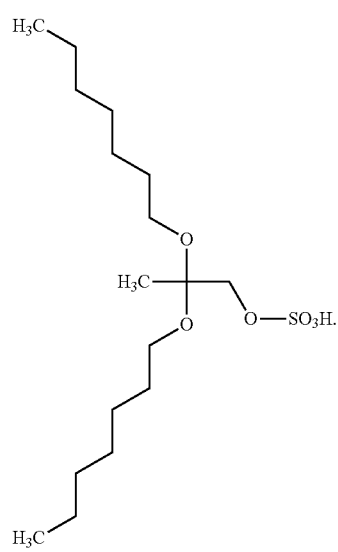 [SMILES: CCCCCCCOC(C)(COS(=O)(=O)O)OCCCCCCC]

2. A cleavable surfactant/detergent compound of the following formula:

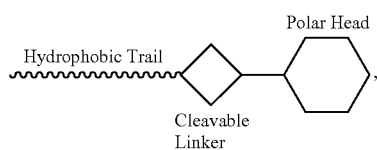

(A) wherein the polar head is chosen from:

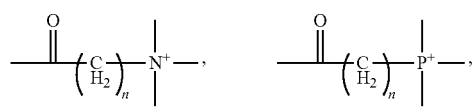

(B) the cleavable linker is chosen from:

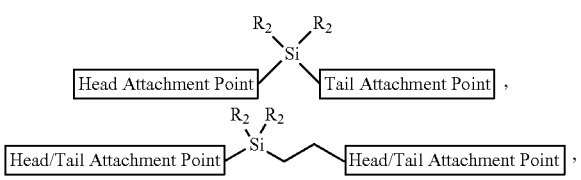

$R_2$ is independently —$CH_3$,

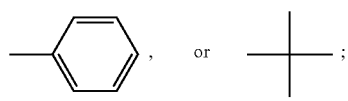

wherein n is an integer from 1 to 12.

3. A method for isolating a hydrophobic molecule, comprising:
providing a plasma comprising a hydrophobic molecule;
applying a cleavable surfactant of claim 2 to the plasma so that the surfactant engages the hydrophobic molecule;

cleaving the surfactant from the hydrophobic molecule; and
analyzing said hydrophobic molecule.

* * * * *